United States Patent
Kelly et al.

(10) Patent No.: US 7,493,264 B1
(45) Date of Patent: Feb. 17, 2009

(54) METHOD OF CARE ASSESSMENT AND HEALTH MANAGEMENT

(75) Inventors: Miriam A. Kelly, Ridgewood, NJ (US); Alan M. Lotvin, Maple Grove, MN (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 867 days.

(21) Appl. No.: 10/166,298

(22) Filed: Jun. 11, 2002

Related U.S. Application Data

(60) Provisional application No. 60/296,772, filed on Jun. 11, 2001.

(51) Int. Cl.
*G06Q 50/00* (2006.01)
(52) U.S. Cl. .................... 705/2; 705/3; 600/300; 600/549; 600/557; 600/587; 600/595; 128/903; 128/904; 128/923; 128/924; 128/925; 455/73
(58) Field of Classification Search ............ 705/2, 705/3; 600/300, 549, 557, 587, 595; 128/903, 128/904, 923, 924, 925; 455/73
See application file for complete search history.

(56) References Cited

U.S. PATENT DOCUMENTS

| | | | |
|---|---|---|---|
| 4,315,309 | A | 2/1982 | Coli |
| 4,667,292 | A | 5/1987 | Mohlenbrock et al. |
| 4,730,259 | A | 3/1988 | Gallant |
| 4,733,354 | A | 3/1988 | Potter et al. |
| 4,839,822 | A | 6/1989 | Dormond et al. |
| 4,878,175 | A | 10/1989 | Norden-Paul et al. |
| 4,945,476 | A | 7/1990 | Bodick et al. |
| 4,987,538 | A | 1/1991 | Johnson et al. |
| 5,018,067 | A | 5/1991 | Mohlenbrock et al. |

(Continued)

FOREIGN PATENT DOCUMENTS

CA 2053553 2/1993

(Continued)

OTHER PUBLICATIONS

Net Gain or Net Loss?, Appleby, Chuck, Trustee; Feb. 1999; 52, 2, p. 20.*

*Primary Examiner*—C Luke Gilligan
*Assistant Examiner*—R. David Rines
(74) *Attorney, Agent, or Firm*—Irah H. Donner; Wilmer Cutler Pickering Hale and Dorr LLP

(57) ABSTRACT

An interactive computer assisted method compiles comprehensive health care information on patients in a central repository, assesses and analyzes this information, and identifies high utilizers of health care services using a computer and a user associated therewith. The method includes the steps of creating a central repository of various databases containing patient information, including demographic information and behavior, and optionally the results of a core survey of health status questions. The invention optionally involves the step of determining the appropriate core questions and the criteria to determine whether and when to ask certain questions of particular patients based on their response to prior questions. The invention accurately predicts risk of a medical condition or progression of a medical condition utilizing an interactive administration of a set of core survey questions combined with diagnostic data and places patients efficiently, reliably, and accurately into the appropriate treatment intervention programs. The invention eliminates redundant, repetitive surveying of patients with multiple medical conditions.

21 Claims, 35 Drawing Sheets

U.S. PATENT DOCUMENTS

| | | | |
|---|---|---|---|
| 5,099,424 A | 3/1992 | Schneiderman | |
| 5,121,496 A | 6/1992 | Harper | |
| 5,193,541 A | 3/1993 | Hatsuwi | |
| 5,225,976 A | 7/1993 | Tawil | |
| 5,235,507 A | 8/1993 | Sackler et al. | |
| 5,235,702 A | 8/1993 | Miller | |
| 5,253,164 A | 10/1993 | Holloway et al. | |
| 5,301,105 A | 4/1994 | Cummings, Jr. | |
| 5,307,262 A | 4/1994 | Ertel | |
| 5,325,293 A | 6/1994 | Dorne | |
| 5,327,341 A | 7/1994 | Whalen et al. | |
| 5,359,509 A | 10/1994 | Little et al. | |
| 5,361,202 A | 11/1994 | Doue | |
| 5,365,425 A | 11/1994 | Torma et al. | |
| 5,414,838 A | 5/1995 | Kolton et al. | |
| 5,482,035 A | 1/1996 | Paloheimo | |
| 5,483,443 A | 1/1996 | Milstein et al. | |
| 5,486,999 A * | 1/1996 | Mebane | 705/2 |
| 5,508,912 A | 4/1996 | Schneiderman | |
| 5,519,607 A | 5/1996 | Tawil | |
| 5,544,044 A | 8/1996 | Leatherman et al. | |
| 5,550,734 A | 8/1996 | Tarter et al. | |
| 5,557,514 A | 9/1996 | Seare et al. | |
| 5,572,422 A | 11/1996 | Nematbakhsh et al. | |
| 5,586,039 A | 12/1996 | Hirsch et al. | |
| 5,594,638 A | 1/1997 | Iliff | |
| 5,598,511 A | 1/1997 | Petrinjak et al. | |
| 5,640,549 A | 6/1997 | Powsner et al. | |
| 5,644,778 A | 7/1997 | Burks et al. | |
| 5,652,842 A | 7/1997 | Siegrist, Jr. et al. | |
| 5,660,176 A | 8/1997 | Iliff | |
| 5,711,297 A | 1/1998 | Iliff | |
| 6,024,699 A * | 2/2000 | Surwit et al. | 600/300 |
| 6,168,563 B1 * | 1/2001 | Brown | 600/301 |
| 6,269,339 B1 * | 7/2001 | Silver | 705/2 |
| 6,294,999 B1 * | 9/2001 | Yarin et al. | 340/573.1 |
| 6,605,038 B1 * | 8/2003 | Teller et al. | 600/300 |
| 2002/0077849 A1 * | 6/2002 | Baruch et al. | 705/2 |
| 2002/0082865 A1 * | 6/2002 | Bianco et al. | 705/2 |
| 2003/0028399 A1 * | 2/2003 | Davis et al. | 705/2 |

FOREIGN PATENT DOCUMENTS

| | | |
|---|---|---|
| CA | 2081737 | 5/1993 |
| CA | 2145935 | 10/1995 |
| EP | 297780 | 6/1988 |
| WO | WO 91/06917 | 5/1991 |
| WO | WO 91/17510 | 11/1991 |
| WO | WO 92/04863 | 4/1992 |
| WO | WO 92/14206 | 8/1992 |
| WO | WO 94/00817 | 1/1994 |
| WO | WO 95/19604 | 7/1995 |
| WO | WO 96/00423 | 1/1996 |
| WO | WO 96/27163 | 9/1996 |
| WO | WO 97/01141 | 1/1997 |
| WO | WO 97/11635 | 4/1997 |
| WO | WO 97/26609 | 7/1997 |

* cited by examiner

| View Conclude Undo Enter Help |
| --- |

Cardiovascular/Respiratory: Thrombophlebitis

Initial Review, Case not yet entered

1 Deep vein thrombosis diagnosed on doppler/venogram [Pass] [Fail] P/F —50

2 Superficial thrombophlebitis diagnosed by exam and one of the following:     No Selection (a) pain
  (b) redness
  (c) swelling
  (d) all of the above 3 Is there proximal embolization?     P/F 4 Anticoagulation therapy contraindicated due to:     No Selection (a) sensitivity to heparin
  (b) GI or intracerebral bleed
  (c) patient has CA or especially metastatic CA

Cardiovascu[lar]  
View Conclude Undo Enter Help  
Initial R[eview]

Treatment  
Recommended = 2A,2B

2A) IV heparin and coumadin (couma[din] be initiated by at least day 2 of heparinization)

2B) Streptokinase or urokinase for 3 followed by 6 days heparin with coumadin initiated by day 2 of heparinization 2C) Bed rest, with or without antibioti[cs] with or without anticoagulants, w[ith] without NSAID'S 4A) Embolectomy or thrombectomy, iliac, femoropopliteal vein by leg incision OT) Other Diagnosis  
PR) Physician review  
PO)

Specialist Review

Case ID#: N/A  
Review #: N/A        Specialist Review #: N/A

ID: [JKEES]

Type:
- ○ Clinical Review
- ● Physician Review
- ○ IME
- ○ Appeal

Reason:
- ☒ Appropriate Treatment Plan
- ☐ Partial Procedure
- ☐ Setting
- ☐ LOS
- ☐ Preop Days
- ☐ Assistant Surgeon
- ☐ Diagnosis Confirmation

[OK] [Cancel] [Print]

DO YOU SMOKE?

YES                                          NO

DO YOU HAVE HYPERTENSION?

HAVE YOU HAD A HEART ATTACK?

DO YOU HAVE HIGH CHOLESTEROL?

DO YOU HAVE DIABETES?

DO YOU HAVE LOWER BACK PAIN OR STRAIN?
ARE YOU ALLERGIC TO ANY MEDICATION?
ETC.

FIG. 26

METHOD OF CARE ASSESSMENT AND HEALTH MANAGEMENT

RELATED APPLICATION

This application claims the benefit of U.S. Provisional Application No. 60/296,772, filed on Jun. 11, 2001, entitled "CARE ASSESSMENT TOOL FOR HEALTH MANAGEMENT", which is hereby incorporated by reference.

BACKGROUND OF THE INVENTION

1. Field of the Invention

The present invention generally relates to a computer implemented and/or assisted process for one or more of eliminating redundant, repetitive surveying of patients with multiple medical conditions, identifying potentially high health care resource utilizers in a population, improving clinical information for use by drug utilization review, care management and prior authorization programs, and/or identifying likely candidates for other health management programs while improving or maintaining the quality of care in a patient population. More particularly, the present invention relates to a computer implemented and/or assisted process for creating a central comprehensive information profile on the health of the patient utilizing, among other sources of information, utilizing medical claims and drug claim files and the interactive selection and/or collection of extensive information on a patient's current health condition, demographics, and risk behaviors. The present invention also relates to assisting, optionally in real-time, the identification of potential drug-disease and drug-drug adverse affects. By combining diagnoses information, vital statistic information and drug claim related information from a variety of internal and external sources and databases, the present invention facilitates the delivery of the highest quality care.

2. Background of the Related Art

Health care costs continue to be a significant portion of the United States Gross National Product, and are still rising. Health care cost containment programs include, among other things, drug utilization reviews ("DUR"), prior authorization of medical care, programs which allow patients to obtain diagnostic advice directly concerning specific problems and the identification and use of intervention programs to prevent future health problems or the progression of disease.

A significant portion of these increased expenses represent costs attributed to individuals who utilize health care services to a higher degree than average. It has been determined that the lack of understanding of the nature and likely needs of such potentially high health care users hinders the ability to target interventions appropriately, and thereby address the medical needs of these individual patients more appropriately.

The administrative cost of enrolling high utilization patients in intervention programs has been high, in part, because patients enrolled in programs to manage inappropriate utilization have been required to complete multiple questionnaires for an overall assessment of health. These questionnaires or surveys are burdensome to the patient and costly for the program. A few of the questionnaires may assess health risk appropriately, but these tools are not designed to, nor predict future resource utilization.

Accordingly, we have determined that many patients are deprived of access to, or the benefit of, the most appropriate health care program and information, which is currently unable to be practically obtained. For example, many people delay in obtaining, or are prevented from seeking, medical attention because of cost, time constraints, or inconvenience. If the health management programs had easy access to updated information on the medical condition of the patient and likely health management needs, many diseases could be more effectively and efficiently treated. Similarly, the early detection and treatment of numerous diseases could keep or prevent many patients from reaching the advanced stages of illness. These advanced stages of illness are a significant part of the costs attributed to our nation's health care system.

To date, no prior art which the inventors are aware of that integrates survey and diagnostic data into a predictive model for high medical resource utilization, create a central portfolio of patient data for assessment of the effects of the health management programs, use this information in providing health care management and prior authorization, and/or identification of and enrollment of candidates for other health management programs. As a way of providing background, some of these other programs are described below.

For example, one prior attempt at a solution to the health care problem is called Ask-A-Nurse, wherein a group of nurses provide health information by telephone around-the-clock. A can call an 800 number 24×7 to obtain health advise from a nurse. The nurse uses a computer for general or diagnostic information on the ailment or complaint mentioned by the caller. The nurse may then refer the caller to a doctor from a computerized referral list for a contracting hospital or group of hospitals. Client hospitals contract with Ask-A-Nurse to provide patient referrals. A managed care option called Personal Health Advisor is similar and adds the capability for the caller to hear prerecorded messages on health topics 24 hours a day.

Several problems exist with these types of prior medical advice systems. First, these systems have high costs associated with having a nurse answer each telephone call. Second, the caller may have to belong to a participating health plan to utilize the service. Third, and significantly, this system is designed to respond to reactive problems determined by the caller, and therefore, provides no ability to eliminate the possibility of such a condition occurring in the first instance, or proactively preventing the condition from occurring. Further, these advice systems are not implementable for large patient populations, particularly where the proactive measures are patient-specific.

However, other inventions are available, such as a computerized service that answers health care questions and advises people in their homes. A health maintenance organization (HMO) may provide this service to its members in a particular geographic area. To get advice at home, an HMO member connects a toaster-sized box to a telephone and calls a toll-free number. Using a keyboard that is part of the box, the user answers questions displayed on a screen of the box relating to the user's symptoms. Depending on the answers, the user might be told to try a home remedy, be called by a nurse or doctor, or be given an appointment to be examined. As with Ask-A-Nurse program, this system is also designed to respond to reactive problems determined by the caller, and therefore, provides no ability to eliminate the possibility of such a condition occurring in the first instance.

At the other end of the spectrum, are various attempts at analyzing retroactively using hindsight, the appropriateness of the delivered medical care for quality and cost. For example, U.S. Pat. No. 5,544,044 to Leatherman et al., incorporated herein by reference, relates to a software-based medical information system that analyzes health care claims records for an enrolled population (e.g., HMO, Medicaid) to assess and report on quality of care based on conformance to nationally recognized medical practice guidelines or quality indicators (See FIGS. 1 through 4, from Leatherman et al.).

The process is typically performed at the request of a customer that is a health maintenance organization, indemnity insurer (e.g., Blue Cross), a large, self-insured employer group or a government program (e.g., Medicaid). The process begins by obtaining the customer specific parameters, such as what time period the customer wishes to analyze or whether the customer wants to have some data broken down by particular providers or other grouping variables 1. The next step 2 updates the system options and parameters using the customer specifications. Thereafter, the system obtains and loads the customer data 3, usually consisting of the customer's already-computerized health care claims data for a specified period, together with enrollment data and health care provider data.

The enrollment data are extracted 4 so as to identify the enrollees served by the customer that meet a predefined enrollment criterion. The resulting enrollment data contains one record per enrollee. Next, the relevant claims data are extracted from the complete customer data base 5 and are configured through linkages to produce the necessary health records. The claims data includes claims records for medical professional services (outpatient records) 6, claims records for hospital services (inpatient records) 7 and claims records for pharmacy purchases (pharmacy records) 8.

If the customer desires, provider-specific data is also extracted from the customer data 9, permitting the later analysis to be broken down by the particular provider of services or products, which may be a particular doctor, clinic or hospital. The resulting files are merged to produce uncorrected master files 11. Duplicate claims are excluded, and claims that have been reversed through the claims adjudication process are also excluded. This produces a master file of health care claims records.

This prior art also involves the application of the definitions for the health care condition to identify the population having that condition, followed by an analysis of the claims records for that population (a subset of the master files) under the defined quality care criteria 12 (FIG. 2).

The result of the analysis is a report that includes: charts and graphs reporting statistically observed quality of care data in the population defined as having the health care condition of interest 13, a written analysis reporting from a care quality viewpoint 14, statistical results considered worthy of highlighting and a report containing recommendations for actions to improve health care quality 15.

Analysis for multiple health care conditions takes place iteratively through the software 16, and the process just described, producing charts, graphs, and reports, using the next health care condition definition to identify the population having that condition, followed by an analysis of the claims records for that population under the defined quality care criteria for that next condition. After all the specified health care conditions have been processed in this manner, the reports for each condition are assembled into a claims-based quality report that is presented to the customer 17.

The system recognizes whether there is the need for detailed analysis. If no such need exists, no further data collection or analysis occurs. However, if a need for detailed analysis of any health care condition has been determined, then the population identified as having that condition is subjected to sampling to determine for which enrollees additional medical records information will be collected 18 (FIG. 3). With the provider's consent, the medical records are abstracted with a particular focus on events that relate to the particular health care condition under study, resulting in a completed medical records abstract form 19.

This abstracted information is then entered into the system via a personal computer to produce a medical record abstract data file 20. Charts and graphs are generated reporting statistically observed data in the population defined as having the health care condition of interest, and a report containing recommendations for actions to improve health care quality is also generated 21 (FIG. 4). If detailed analysis of medical records is specified for multiple health care conditions, then the preceding steps are repeated until charts and graphs reporting statistically observed data and a report containing recommendations for actions to improve health care quality are developed for each health care condition 22.

After all the specified health care conditions have been processed in this manner, the reports for each condition are assembled into a detail level report that is presented to the customer and the process ends 23. One major drawback of this system is that, for example, it analyzes "after-the-fact" the appropriateness of the delivered medical care for quality and cost. Further, the Leatherman et al. system is focussed on the appropriateness of medical costs for the preferred service, and does not determine patient specific services and/or patient specific future/proactive treatment prior to occurrence of medical conditions on a patient-specific basis.

U.S. Pat. No. 5,660,176 to Iliff, incorporated herein by reference, is directed to a computerized medical diagnostic and treatment advice system. Referring to FIG. 5, the components of the computerized medical diagnostic and treatment advice system are shown. A personal computer (PC) includes a plurality of components within an enclosure. A plurality of telephone lines 24 interface the public telephone network to the computer. One of telephone lines 25 is shown to be switched via network to connect with a telephone that is used by a person desiring to speak with a medical advice user 26.

The system runs on the PC with a microprocessor 27. Telephone functions use a voice processing board (VP) 28 based on a digital signal processor (DSP). A group of one to four telephone lines 29 connect to the voice processing board 28. The computer may include a plurality of VP boards based on how many phone line connections are desired for the system. Speech recognition is achieved using Voice Processing Corporation's speech recognition VPRO-4 board (voice recognition board or VR board) (which is also DSP based) 30.

The VR board 30 and the VP board 28 both connect to an industry standard architecture (ISA) bus 31. The VP board also connects to a VPRO-Adapt board 32 via an analog audio bus that is called Analog Extension Bus 33. The Adapt board further connects to a digital audio bus 34. The VR board also connects to the digital audio bus. The Adapt board performs analog to digital signal conversion to a digital pulse code modulation (PCM) format.

A video adapter board 35 interconnects to a video monitor 36. A serial communication circuit 37 interfaces a pointing device, such as a mouse 38. A parallel communication circuit may be used in place of the serial communication circuit 37 in another embodiment. A keyboard controller circuit 39 interfaces a keyboard 40. A small computer systems interface (SCSI) adapter 41 provides a SCSI bus 42 to which a 500 Mb or greater hard disk drive 43 is attached.

The hard drive stores database files such as the patient files, speech files, and binary support files. Main memory 44 connects to the microprocessor 27. An algorithm processor 45 includes a parser and supporting functions that manipulate a memory variable symbol table and a run time stack.

FIG. 6 is a block diagram illustrating a conceptual view of the database files and processes of the system from Iliff. Patient log in process 46 (FIG. 6) is used to identify a patient who has previously registered into the system. An assistant log in process 47 is used to identify an assistant who has previously registered into the system.

If the caller is the patient, a patient registration process 48 is used to register new or first-time patients. If the caller is not the patient, an assistant registration process 49 is used to register new or first-time assistants. Then, if the patient is not already registered, an assisted patient registration process 50 is used to register the patient.

The master patient and assistant enrollment database 51 is created at run-time by one of the registration processes. This database is read by the patient log in process 46 to validate a patient's identity at log in time, and by the assistant login process 47 to validate an assistant's identity at log in time. The database is essentially a master file of all registered patients and assistants indexed by their patient ID number or assistant ID number, respectively.

In Iliff, the medical advice is provided to the general public over a telephone network 24. Two new authoring languages, interactive voice response and speech recognition, are used to enable expert and general practitioner knowledge to be encoded for access by the public. Meta functions for time-density analysis of a number of factors regarding the number of medical complaints per unit of time are an integral part of the system. Thus, the system in Iliff, for example, is designed as a reactive measure to respond to caller complaints, and provides no process for ensuring and/or designing appropriate patient specific care, nor collects extensive information on a patient's use of medication(s), medical history, and/or satisfaction.

U.S. Pat. No. 5,557,514 to Seare et al., incorporated by reference, provides a mechanism for assessing medical services utilization patterns. The program achieves this object by allowing comparison processing to compare an individual treatment or a treatment group against a statistical norm or against a trend. Seare et al. also provides a mechanism for converting raw medical provider billing data 52 (FIG. 7) into an informative historical database 53. The program achieves this object by read, analyze and merge ("RAM") processing 54 coupled with claims edit processing 55 to achieve a reliable, relevant data set. It provides a mechanism for accurately determining an episode of care. The program achieves this object by providing a sequence of steps which, when performed, yield an episode of care while filtering out irrelevant and inapplicable data. Further, Seare et al. provides a method for performing a look-up of information, that is, providing a mechanism for gaining access to different parts of the informational tables maintained in the database 53. This object is achieved by reviewing the referenced tables for specific codes representing specific diagnoses. The codes are verified for accuracy. Then tables are accessed to display selected profiles. Users are then given the opportunity to select profiles for comparison.

Searle et al. provides a method for comparing profiles. This object is achieved by comparing index codes against historical reference information stored in the parameter tables 54 (see FIG. 8). Discovered information is checked against defined statistical criteria in the parameter tables 55. The process is repeated for each index code and its profile developed in the history process as many times as necessary to complete the information gathering 56. The system creates, maintains and presents to the user a variety of report products 57. These reports are provided either on-line or in a hard copy format. The process of creating, maintaining and presenting these reports is designed to present relevant information in a complete and useful manner.

FIG. 9 from Searle et al. depicts steps performed in the method to establish a practice parameter or utilization profile for a particular diagnosis. Searle et al. includes both a system and a method for analyzing health care providers' billing patterns, enabling an assessment of medical services utilization patterns. Searle et al. determines whether a provider or multiple providers are over utilizing or underutilizing services when compared to a particular historical statistical profile. The statistical profile is a statically derived norm based on clinically-validated data which has been edited to eliminate erroneous or misleading information. The profiles may be derived from geographic provider billing data, national provider billing data, the provider billing data of a particular pay or entity (such as an insurance company) or various other real data groupings or sets. Twenty informational tables are used in the database of Searle et al. including a Procedure Description Table, ICD-9 Description Table, Index Table, Index Global Table, Index Detail Table, Window Table, Procedure Parameter Table, Category Table, Qualifying Master Table, Specialty Table, Zip/Region Table, Family Table, Speciality Statistic Table, Age/Gender Statistic Table, Region Statistic Table, Qualifying Index Table, Qualifying Group Table, Category Parameter Table, Duration Parameter Table and Family Table. Thus, Searle et al. includes similar disadvantages as the other referenced prior art references, analyzing past medical conditions, and the appropriateness therefor.

International Patent Application Publication No. WO 95/1904 by Tallman et al., incorporated herein by reference, provides a medical network management system and process system based on understanding and managing the process of care, in an integrated manner, from the onset of patient perception of possible needs. This prior art provides such a medical network management system and process which allows beneficiaries to obtain appropriate care, at the appropriate time, from an appropriate provider. It also provides such a medical network management system and process which effectively reduces utilization and costs, while increasing user satisfaction and overall quality of care. Tallman et al. provides a medical network management system and process which uses information systems to help guide patients through and manage the process of care, thereby assuring quality health care.

Nurses search the information using the criteria necessary to meet specific patient needs as identified through the assessment process. The process begins when the patient initiates a call or visits a nurse utilizing the NMS (network management system) 58 (see FIG. 10). Patient information is gathered and eligibility is confirmed by accessing data from a patient chart 59. A determination is then made whether the patient requires medical intervention, using the algorithms 60. If medical intervention is not required, home care instructions are provided 61 and a follow-up call is scheduled 62. During follow-up, a determination is made whether the problem has been resolved safely. If not, another determination is made whether medical intervention is required 63.

The medical network management system in Tallman et al. has a data processing system, including a memory (containing a patient assessment stored program and a patient database), a display, and input means. The patient assessment stored program 65 (FIG. 11) includes means for checking patient eligibility, means for selecting a branched chain logic algorithm for assessing a patient for an appropriate timing and type of medical care, and a plurality of branched chain logic algorithms. Each of the branched chain logic algorithms (see FIGS. 12, 13, and 14, for example) assess the patient for an appropriate timing and level of medical care. The data processing system is configured by the patient assessment stored program to present a series of questions on the display for checking patient eligibility to receive medical care, for selecting one of the plurality of branched chain algorithms, for guiding the patient through the selected one of the plurality of branched chain algorithms, to enter answers from the patient to the series of questions, to make a medical care timing and level of medical care recommendation in response to patient answers to the questions, and to provide the medical care timing and level of medical care recommendation on the display.

A first series of questions is presented on the display 68, 69, 70 (FIG. 12) to select one of a plurality of branched chain algorithms 71-76 which assess the patient for an appropriate timing and level of medical care. A second series of questions is presented on the display to guide the patient through the selected one of the plurality of branched chain algorithms 71-76. Answers from the patient to the second series of questions are entered in the data processing system. A medical care timing and level of medical care recommendation is made in response to patient answers to the second series of questions.

This set of information tools are used by health care professionals to assess patient conditions and assist in the selection of health care services and to help patients find appropriate care at the appropriate time. The comprehensive, automated set of proprietary assessment algorithms (for example, FIGS. 12, 13, and 14) enable a trained nurse to sort patients into different risk categories, safely and effectively by requiring a medical diagnosis. Patients can then be guided to an appropriate level and type of care for their problem(s) based on their level of risk and set of potential needs.

To understand risk sorting, consider 10,000 beneficiaries of members of a health plan. In a year, almost 1000 members of this group will become patients seeking medical care for lower back pain symptoms. Among those who receive care, there will only be a very small number of patients whose pain actually results from serious, but infrequent causes/health conditions. A series of questions, asked in the correct order, can clearly identify those patients for whom these serious causes cannot be safely eliminated. They must all receive immediate, proper medical care to actually search for any of these conditions and potentially prevent very serious consequences.

Once these patients with potential infrequent problems are identified, the remaining patients are those almost certainly experiencing some form of musculo-skeletal back pain, which is almost always self-limiting and self-correcting. None are in immediate danger of death or further injury. If symptoms persist, a higher level of medical care could then be appropriate. Through the process of asking questions and sorting patients by risk categories, safe and apparently effective treatment are claimed.

When any of the algorithms indicate that medical intervention is appropriate for a given patient, the nurse will then use the second major component of the NMS, which is described below, to assist that patient in selecting an appropriate, individual provider.

The second major component of the system consists of a proprietary relational database 66 (FIG. 11) which contains the information necessary to effectively differentiate the various providers participating in a given network and to manage the patient flow into their practices. This system component enables the nurse to help patients select an individual doctor, clinic, or hospital; i.e., an appropriate provider of the services required to meet their needs. The patient assessment component and the provider information component are linked by provider codes 67, which identify by standard procedure billing codes, what procedures the different providers perform in the normal course of their practice. The link further includes patient information, such as sex, age, zip code, health plan and other patient information useful for matching a patient to a provider.

Data describing areas of clinical expertise and the practice in general, are collected from each provider. This information is monitored and updated regularly. It can also be augmented by relevant information from other sources such as claims data and can contain items such as procedural frequency or clinical outcomes. Thus, Tallman et al. is principally based on the patient awareness of medical needs. Tallman et al. thus assumes that knowledge about a condition results in planned action to seek care. The literature is clear that, for many individuals, this is poorly correlated. In other words, Tallman et al. is a more sophisticated approach at reactively responding to medical conditions.

International Patent Application Publication No. WO 94/00817 by G. Mcilroy et al., provides a health care management data processing system that is a real-time, interactive system to manage the health care process. The system can be used by hospitals, physicians, insurance companies, HMOs, and others in the health care field to promote cost-effective health care.

The Mcilroy et al. system builds from a data base of treatment guidelines developed by medical professionals (see FIG. 15). It provides a diagnosis-based system that can be used during various steps of the clinical decision process: (1) prospectively, before treatment, when an individual presents a health concern; (2) concurrently, at any stage of existing treatment; and (3) retrospectively, after treatment as been provided. The treatment guidelines are structured to work with an interactive question and answer methodology that ensures that the most appropriate data are collected, and guides the user through the complex medical evaluation process. This is done by presenting questions in a logically structured order from the condition, leading to guideline-recommended treatment 77 (FIG. 16). The information retained by the system allows for a consistent, efficient review process. Variances between actual or proposed and guideline-recommended treatment can be used for quality assurance and audit purposes. Also, cross-specialty review is facilitated.

There is a processing unit 78 (FIG. 17) and software-implemented health condition and treatment guidelines program 79. A user inputs 80 an individual's health data into a new or existing case file (FIG. 18) in response to inquires implemented in a health condition specific guideline. Through the interactive guideline query-response process, a guideline-recommended treatment (or treatments) is obtained (FIG. 19). The user may adopt or accept the guideline-recommended treatment or input an actual or proposed treatment that is different. Discrepancies between actual/proposed and guideline-recommended treatment are identified and the user's choice is documented through interactive queries. Once a treatment is selected, the case information is added to the data base and an additional reviewer can analyze the file. The case may be re-opened, and changes may be made at any stage in the process to reflect new conditions, or new or modified treatments.

At the foundation of the system is a set of diagnosis-based guidelines that are derived from medical, professional and health care management expertise (FIG. 15). Each guideline is associated with a particular health care condition for which treatment exists. Each guideline is intended to lead a system user through a sequence of interactive data collection queries based on the specified health care condition observed in an individual patient. The data-collection queries are logically structured so that the user identifies pertinent patient characteristics and is led to an endpoint that is usually one recommended treatment (see e.g. FIG. 16). However, the endpoint may also be two or more alternative treatments, a pointer to a different guideline or a recommendation for further clinical evaluation before treatment is selected.

As implemented in the system, a guideline can be viewed as a decision tree with multiple data collection nodes (FIG. 16 and FIG. 18), most of which have conditional branching to connected nodes based on user-supplied data. The endpoints of navigation through the decision tree are usually embodied in a set of recommended treatments (e.g., FIG. 19). The path to any recommended treatment involves one or more conditional branches. Thus, each guideline implemented in the system has a definite algorithmic structure that guides the user. Mcilroy et al. therefore is more centrally focused on practice health care, and/or assisting a clinician during the diagnosis and/or treatment of the patient.

Accordingly, after review of the prior art and the needs of the health care system, we have determined that it is desirable to provide a method and/or system to facilitate the delivery of high quality services to high health resource utilizers in a population.

It has also been determined that it is desirable to provide a method and/or system that eliminates and/or manages redundant, repetitive, medical and/or pharmaceutical related information for better utilization of resources in conducting same.

It has also been determined that it is desirable to provide a method and/or system that identifies dynamically or in real-time candidates for other health care management programs.

We have also determined that it is desirable to provide a method and/or system that improves the clinical information for use in patient specific drug utilization review, care management, and prior authorization programs, improving the overall quality of care provided.

We have also determined that it is desirable to provide a method and/or system that provides a central portfolio of patient specific data for assessment of the effects of health management programs through the selection and/or collection of extensive information on patient specific medical claims, drug claims, an interactive interview and/or demographic information.

We have also determined that it is desirable to have a method and/or system that incorporates lifestyle and/or psychosocial indicators with clinical data to more effectively tailor health care messages and to change behavior.

We have also determined that it is desirable to provide a computer implemented and/or assisted process for creating and administering a set of core patient specific survey questions and combining the patient specific information obtained from the single survey or multiple surveys with patient specific diagnostic data to accurately predict risk of an event or progression advancement in medical conditions which are likely to result in high utilization of health resources in an efficient and timely manner for a pre-selected and/or targeted sub-patient population from one or more larger patient populations, health care organization groups and the like.

SUMMARY OF THE INVENTION

It is therefore a feature and advantage of the present invention in providing a method and/or system to identify or target potentially high health resource utilizers in a population, and to enlist them in the appropriate utilization of healthcare resources.

It is another feature and advantage of the present invention in providing a method and/or system to efficiently, reliably, and accurately place patients into the appropriate treatment intervention.

It is another feature and advantage of the present invention in providing a method and/or system to create a consolidated repository of patient information from all sources, including drug claims, medical claims, interactive surveys, and/or diagnostic tests.

It is another feature and advantage of the present invention in providing a method and/or system that eliminates redundant, repetitive surveying of patients with multiple medical conditions and/or multiple pharmaceutical related issues.

It is another feature and advantage of the present invention in providing a method and/or system that provides improved clinical information for use in care management, drug utilization review, identification of intervention programs, and in program evaluation.

It is another feature and advantage of the present invention in providing a method and/or system that identifies candidate patients from within a target population and determines their eligibility for other health management programs which will enhance the health care of those individuals.

It is another feature and advantage of the present invention in providing a method and/or system that solicits and/or infers those psychological factors (internal drivers) to effectively change behavior.

It is another feature and advantage of the present invention in providing a method and/or system that provides an efficient and effective method of enrolling patients in other health management programs which will enhance the health care of those individuals.

It is another feature and advantage of the present invention in providing a method and/or system that improves the patient-specific clinical and/or medical information for use by drug and/or medical utilization review, care management, and prior authorization programs.

It is another feature and advantage of the present invention in providing a method and/or system that provides a central portfolio of patient data for assessment of the effects of health management programs.

It is another feature and advantage of the present invention in providing a method and/or system that accurately predicts one or more patient-specific risks of a medical condition utilizing an interactive administration of a set of core survey questions combined with diagnostic data.

It is another feature and advantage of the present invention in providing a method and/or system that accurately predicts one or more patient-specific risks of a progression of a medical condition utilizing an interactive administration of a set of core survey questions combined with diagnostic data.

It is another feature and advantage of the present invention in providing a method and/or system that accurately predicts a resulting high utilization of health resources via an interactive administration of a set of core survey questions combined with diagnostic data.

It is another feature and advantage of the present invention in providing a computer implemented and/or assisted process for identifying and/or measuring high utilizers of health care in a population, through the selection and/or collection of information on a specific patient's medical condition, utilizing a set of core survey questions administered interactively and combined with diagnostic data.

It is another feature and advantage of the present invention that the selection and/or collection of specific information on a patient's medical condition may be obtained by administering interactively a set of core survey questions as a result of a patient calling in over the telephone, the provider calling the patient, the patient responding from home via the internet, the patient being interviewed live in a doctor's office or other location, the patient responding on a computer terminal in the doctor's office or some other location, and/or the patient responding by mail.

The present invention is based, in part, on our discovery of the greatly enhanced benefits resulting from combining a core set of survey questions, interactive administration of the questions, and review of diagnostic data. We have also discovered that exceptional results in terms of patient health are possible when high utilization patients are identified and provided proactive advice, medical treatment and/or during treatment.

It has also been discovered that an important feature of the present invention is a computer implemented process of administering the core set of questions and combining this resulting patient-specific information with existing diagnostic data to benefit the patient. The implementation and/or assistance of the computer for the process and system described herein greatly facilitates the efficient implementation of the present invention.

The Health Assessment Questionnaire (HAR) of the present invention (hereinafter HAQ) is a health status tool designed to gather responses from a core set of survey questions. The tool may include paper copy, over the telephone, the Internet, by mail, by touch screen at a kiosk or in the doctor's office or otherwise and compile all available patient information in a central repository. The review provides, for example, an evaluation of overall health, an identification of conditions that limit moderate day-to-day activities, lifestyle risk factors, behavioral indicators, vital statistics (e.g., height, weight, and the like), identification of emotional state, allergies, smoking status, and/or name and telephone number of the personal physician.

The HAQ's primary goals are to eliminate redundant, repetitive surveying of patients, optionally with multiple medical conditions, to collect self reported drug and allergy data, to capture lifestyle and behavioral information to develop more meaningful messages to individuals, and to predict patients who are potentially high utilizers of health care services. The HAQ's secondary goals are to identify health risks or progression of existing conditions, identify candidates for other health care programs, and improve the clinical information for use by DUR, demand management, and prior authorization programs improving the overall quality of care provided. This patient assessment process ensures appropriate patient care through the collection of extensive information on the factors which are likely to result in high utilization of health care services. For example, but without limitation, information is gathered on existing health-related limitations on physical activity, weight and height, smoking status, emotional state, quality of life, functional status, allergies, presence of back pain, hypertension, occurrences of heart attacks or angina, cholesterol levels, and/or diabetes, as well as collection of diagnostic and/or lifestyle information on the patient.

To achieve the above and other features and advantages of the present invention, an interactive computer assisted method allows a patient to call an interviewer at a central location to request responses to medical questions, and allows the interviewer who responds to select the appropriate core questions about the patients health status, and obtain the relevant patient-specific answers from the patient. The invention also combines these answers with diagnostic data, and the results are analyzed using a computer by a user associated therewith.

The HAQ yields a patient profile for individual patients, creating an index of drug claims, demographic data, and program eligibility data, administering the core survey questions and/or updating the survey periodically, converting the answers to codified information, such as coded information, generating one or more lists of other health programs which can be offered, prioritizing such programs, and updating the individual patient's profile. The method also includes the steps of enrolling the patient in new programs based on the interactive survey, where appropriate. The method also includes the steps of preliminarily evaluating, by the computer, whether the patient has the potential to be a utilizer of health care services, and determining whether the patient has a health risk or progressive condition that requires medical attention.

In accordance with another embodiment of the invention, an interactive computer assisted method allows an interviewer to call a patient, select the appropriate core questions based on the information obtained from a central patient profile stored in a central computer, and obtain the relevant answers from the patient. Then, these answers are combined with diagnostic data, and the results are analyzed using a computer by a user associated therewith. The method includes the steps of creating a patient profile for individual patients in the program, creating an index of drug claims, demographic data, and program eligibility data, administering the core survey questions and/or updating the survey periodically, converting the answers to information, generating one or more lists of other health programs which can be offered, prioritizing such programs, and updating the individual patient's profile.

The method also includes the steps of enrolling the patient in new programs based on the interactive survey, where appropriate, and preliminarily evaluating, by the computer, whether the patient has the potential to be a high utilizer of health care services. The method also includes the steps of determining whether the patient has a health risk or progressive condition that requires medical attention.

In another embodiment of the invention, an interactive computer assisted method allows a patient to contact an interviewer through an interactive touch screen or keyboard in a doctor's office or elsewhere to ask questions, provide the necessary information, and receive advice, if necessary. Upon contact via a computer line from the touch screen or key board, the interviewer selects the appropriate core questions based on the information obtained from a central patient profile stored in a central computer, and obtains the relevant answers interactively from the patient. Then these answers are combined with diagnostic data, and the results are analyzed using a computer by a user associated therewith.

The method includes the steps of creating a patient profile for individual patients in the program, creating an index of drug claims, demographic data, and program eligibility data, administering the core survey questions and/or updating the survey periodically, converting the answers to information, generating one or more lists of other health programs which can be offered, prioritizing such programs, and updating the individual patient's profile.

The method also includes the steps of enrolling the patient in new programs based on the interactive survey, where appropriate, preliminarily evaluating, by the computer, whether the patient has the potential to be a low, medium or high utilizer of health care services. The method also includes the steps of determining whether the patient has a health risk or progressive condition that requires medical attention.

Yet another embodiment of the invention involves the use of an interactive computer assisted method which allows an interviewer to call a patient, select the appropriate core questions based on the information obtained from a central patient profile stored in a central computer, and obtain the relevant answers. Then these answers are combined with diagnostic data, and the results are analyzed using a computer by an user associated therewith. The method includes the steps of creating a patient profile for individual patients in the program, creating an index of drug claims, demographic data, and program eligibility data, administering the core survey questions and/or updating the survey periodically, converting the answers to information, generating one or more lists of other health programs which can be offered, prioritizing such programs, and updating the individual patient's profile. The method also includes the steps of enrolling the patient in new programs based on the interactive survey, where appropriate. The method also includes the steps of preliminarily evaluating, by the computer, whether the patient has the potential to be a utilizer of health care services. The method also includes the steps of determining whether the patient has a health risk or progressive condition that requires medical attention.

A further, different embodiment of the invention allows a person who is designated to maintain the central repository of patient profiles to contact a pre-selected group of patients to perform an interactive, computer assisted method to update and maintain a complete patient health profile. This designated person utilizes a mail survey, the core survey of questions, computerized input of the results, and a mail or telephone follow up interview. Once a completed survey is returned, a central record of a patient's health profile information is created. The interviewer pre-selects patients to have their profile updated, and pre-selects the appropriate core questions based on the information obtained from a central patient profile stored in a central computer. The patient optionally receives the mail survey, provides the relevant answers, and returns the questionnaire to the designated person. The data are inputted or scanned into a computer maintained central patient profile repository via a key board, scanning device or other device. Then these answers are combined with diagnostic data, and the results are analyzed using a computer by a user associated therewith.

The method includes the steps of creating a patient profile for individual patients in the program, creating an index of drug claims, demographic data, and program eligibility data, administering the core survey questions and/or updating the survey periodically, converting the answers to information, generating one or more lists of other health programs which can be offered, prioritizing such programs, and updating the individual patient's profile.

The method also includes the steps of enrolling the patient in new programs or offering other new opportunities based on the interactive survey, where appropriate. The method also includes the steps of preliminarily evaluating, by the computer, whether the patient has the potential to be a high, medium or low utilizer of health care services. The method also includes the steps of determining whether the patient has a health risk or progressive condition that requires medical attention.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These, together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

FIG. 18 is a prior art exemplar of the questions asked for thrombophlebitis condition and the pass and fail criteria;

FIG. 19 is a prior art exemplar of the treatment recommendation options available in the expert system for a specialist's review of a cardiovascular condition;

FIG. 23 is a block diagram illustrating a conceptual view of the process of creating the central repository of patient profiles of the system in FIG. 21a;

FIG. 24 is a block diagram illustrating a conceptual example of an expert system like the systems used to derive the core survey and determine high utilizers of the system in FIG. 21a;

FIG. 26 is a block diagram illustrating examples of interactive core questions used in the computerized Care Assessment Tool system of the present invention;

FIG. 27 is a block diagram illustrating the steps in the high utilizer expert system described in FIG. 21a;

NOTATIONS AND NOMENCLATURE

Figure 1:
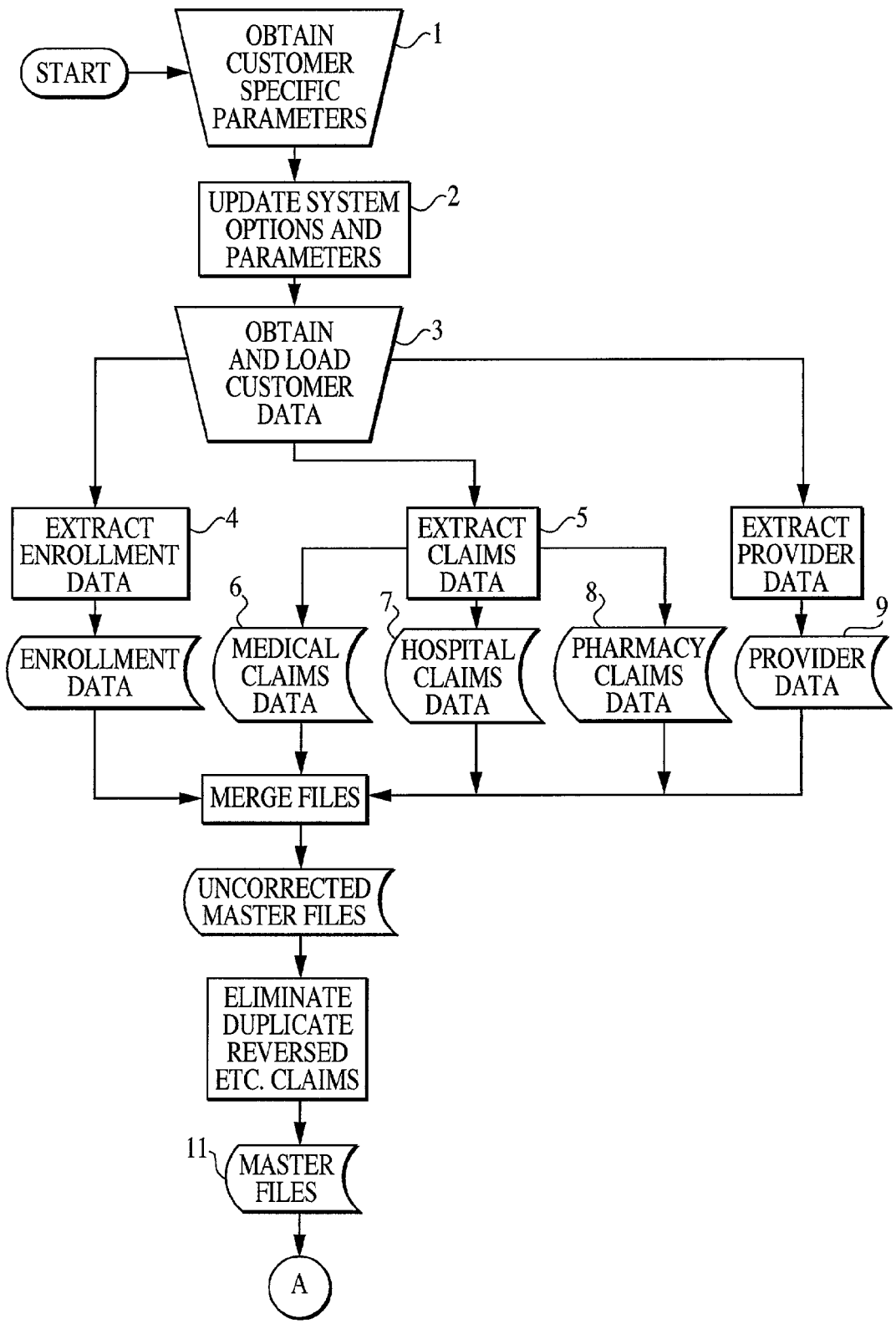
FIG. 1 is a prior art flow chart depicting the steps used to create master files from enrollment data, medical claims data, hospital claims data, pharmacy claims data, and provider data.
Figure 2:
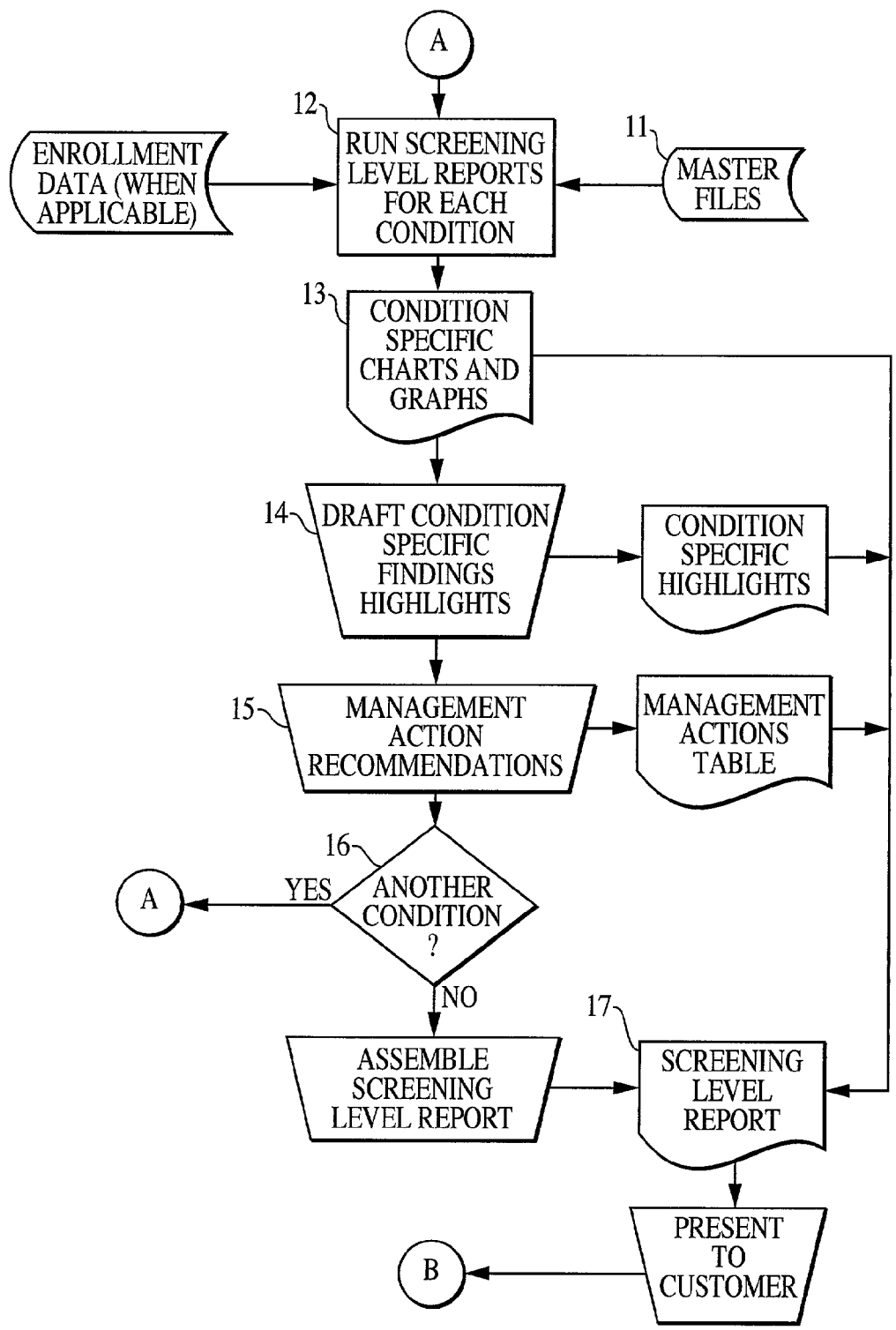
FIG. 2 is a prior art flow chart that depicts the process of running screening reports, creating condition specific charts, determining condition specific findings, and management action recommendations, and screening level reports for customers.
Figure 3:
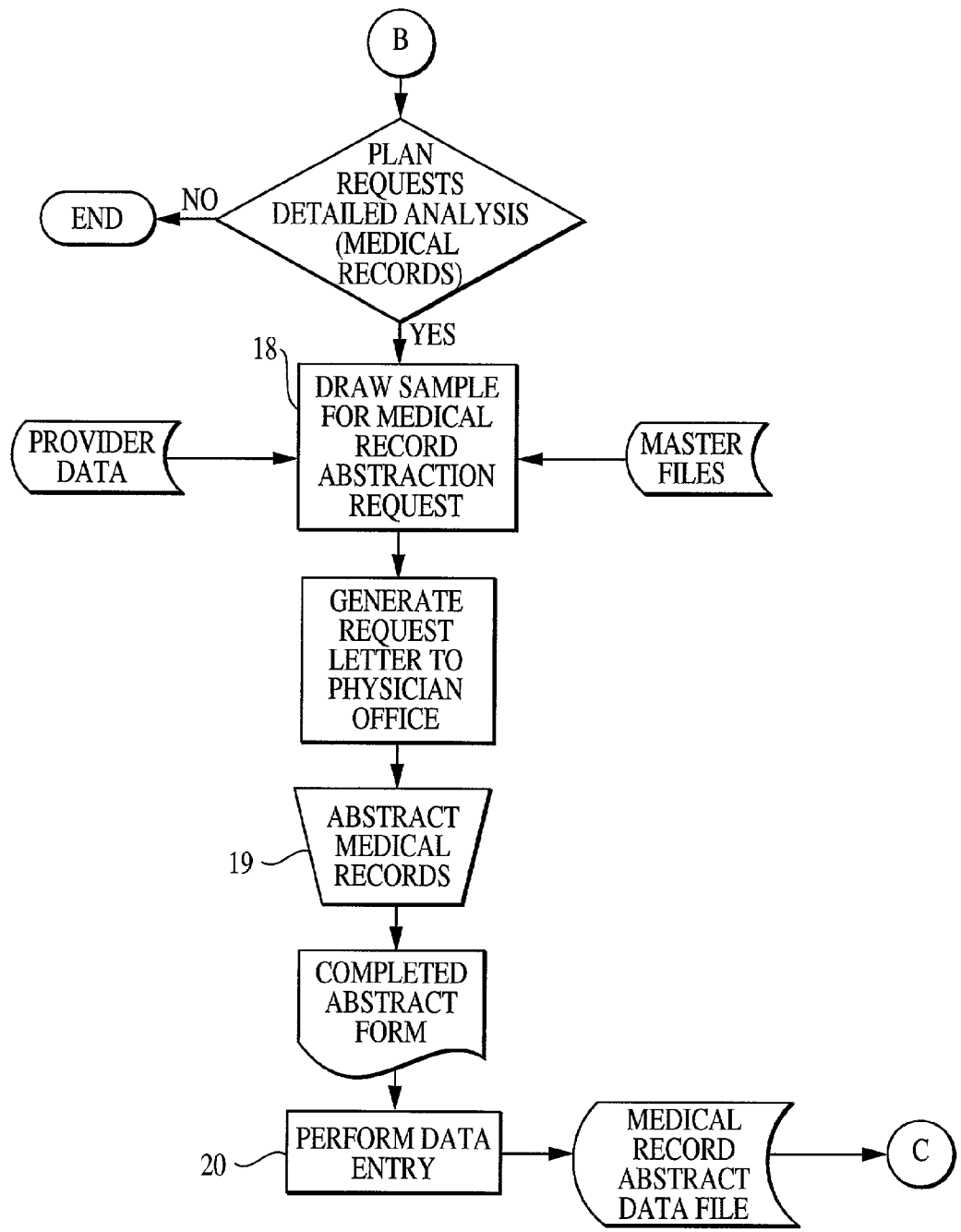
FIG. 3 is a prior art flow chart that depicts process of combining detailed analysis of medical records with provider data to create abstraction requests, general request letters to physicians, and create medical record abstract data file.
Figure 4:
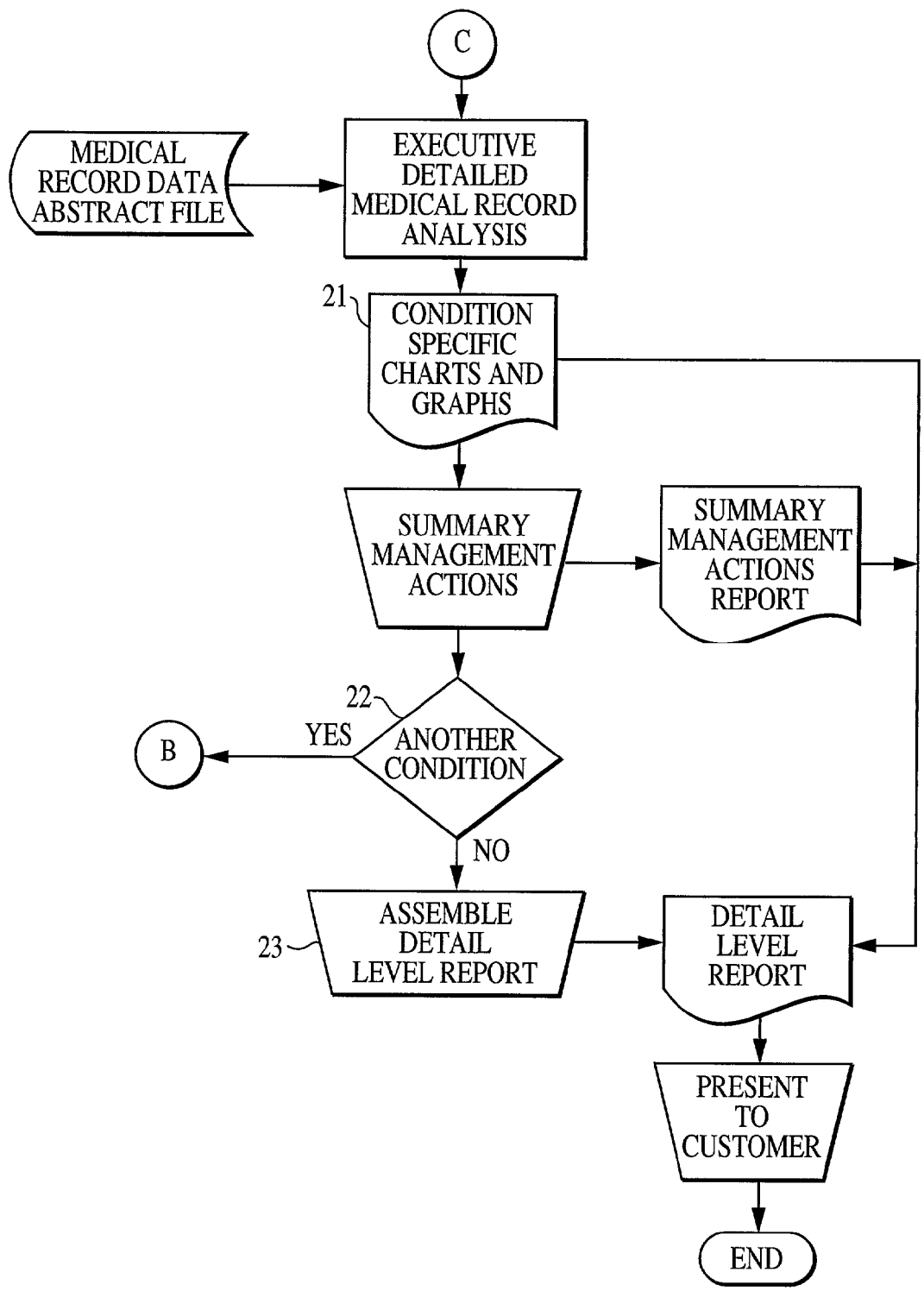
FIG. 4 is a prior art flow chart depicting the creation of an executive detailed medical analysis from medical record data abstract file, condition specific charts and graphs, summary management actions and reports, detailed level reports for customers.
Figure 5:
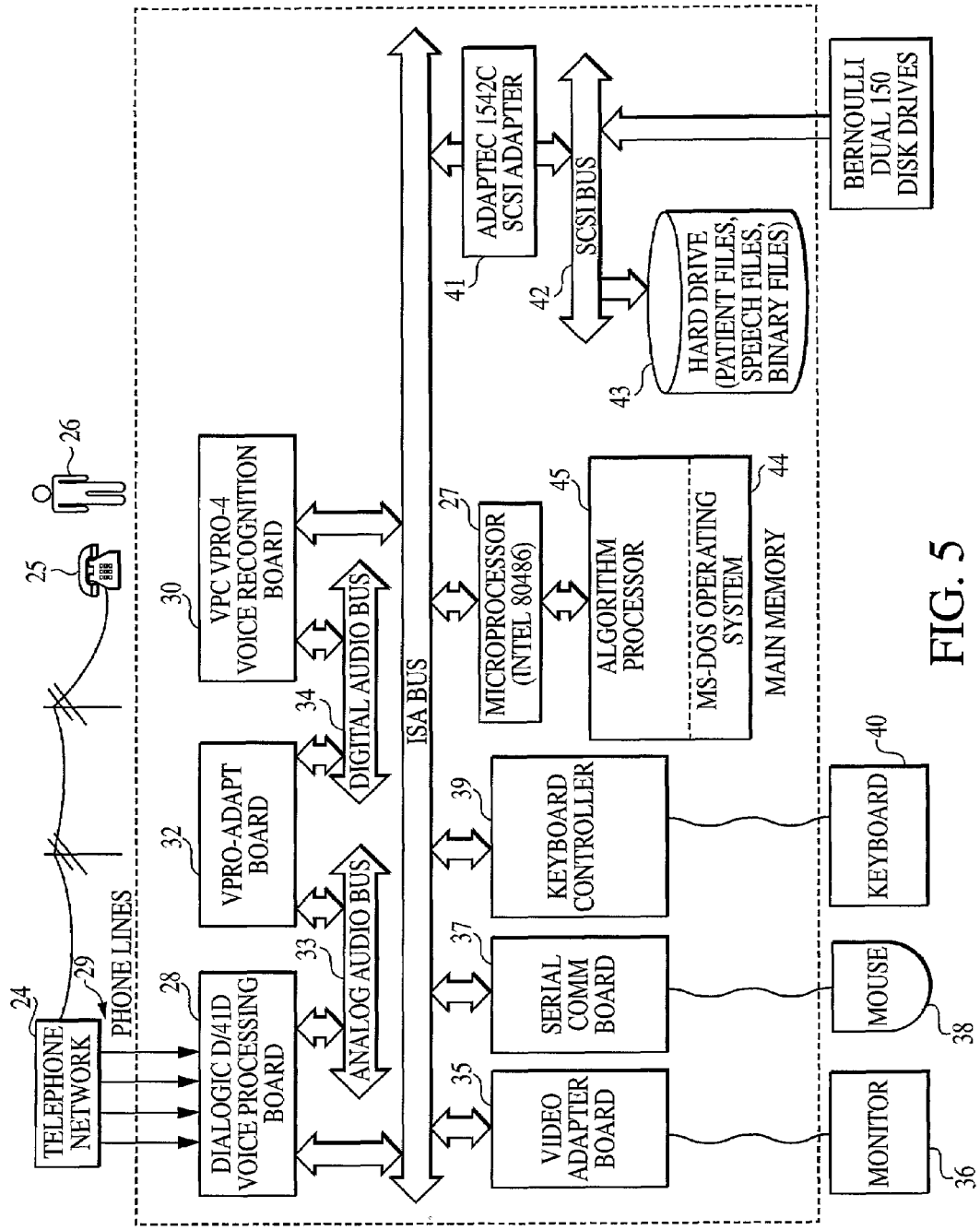
FIG. 5 is a prior art block diagram showing hardware system from the telephone network, voice processing boards, video adapters, keyboards, microprocessor, algorithm processor, and hard drive used to process the patient and assistant enrollment evaluation process of this prior art.
Figure 6:
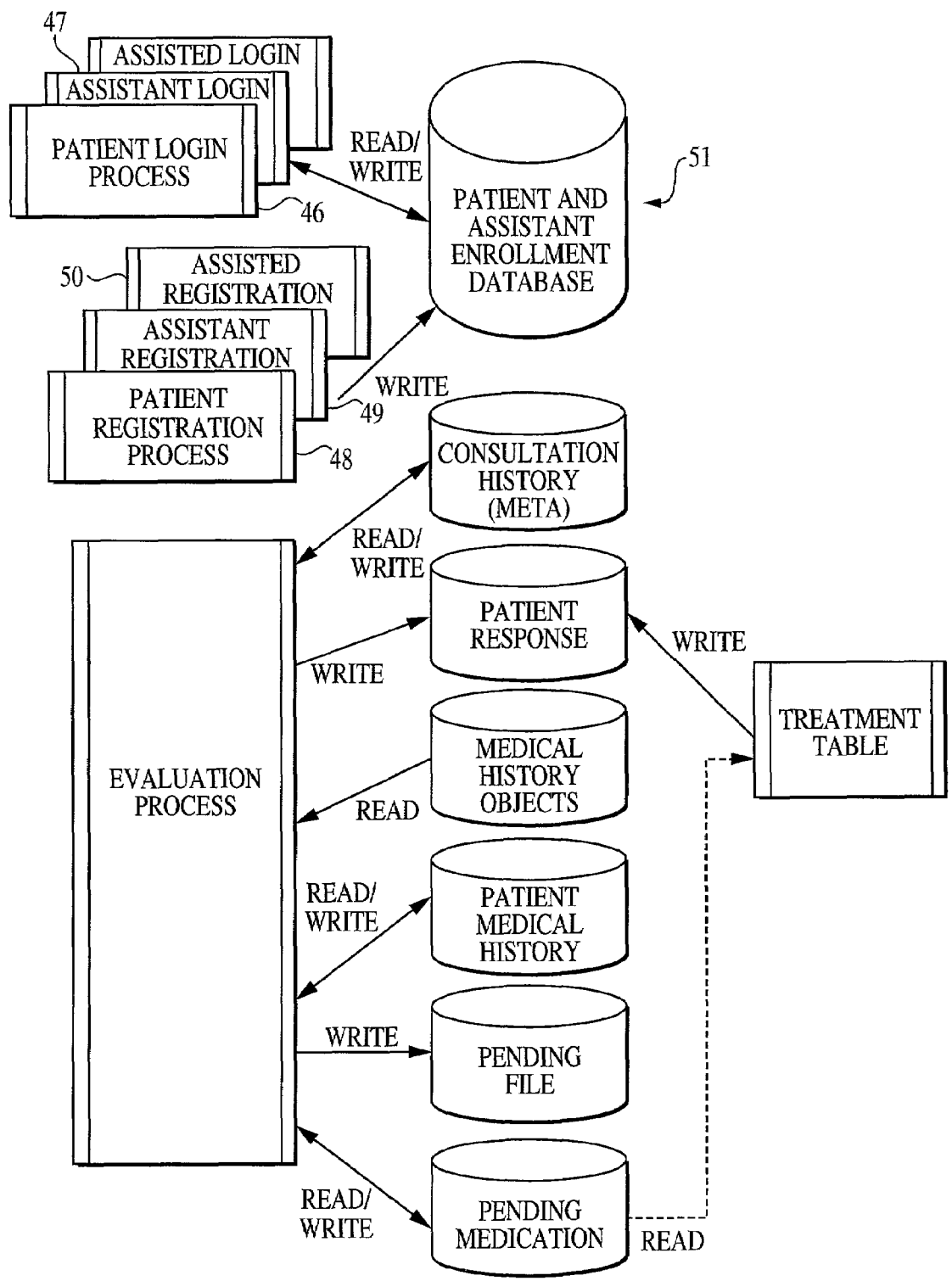
FIG. 6 shows the conceptual software used in a prior art method to register a patient, obtain information from the patient and assistant enrollment database, evaluate the patient's response and history, and determine treatments from the treatment table.
Figure 7:
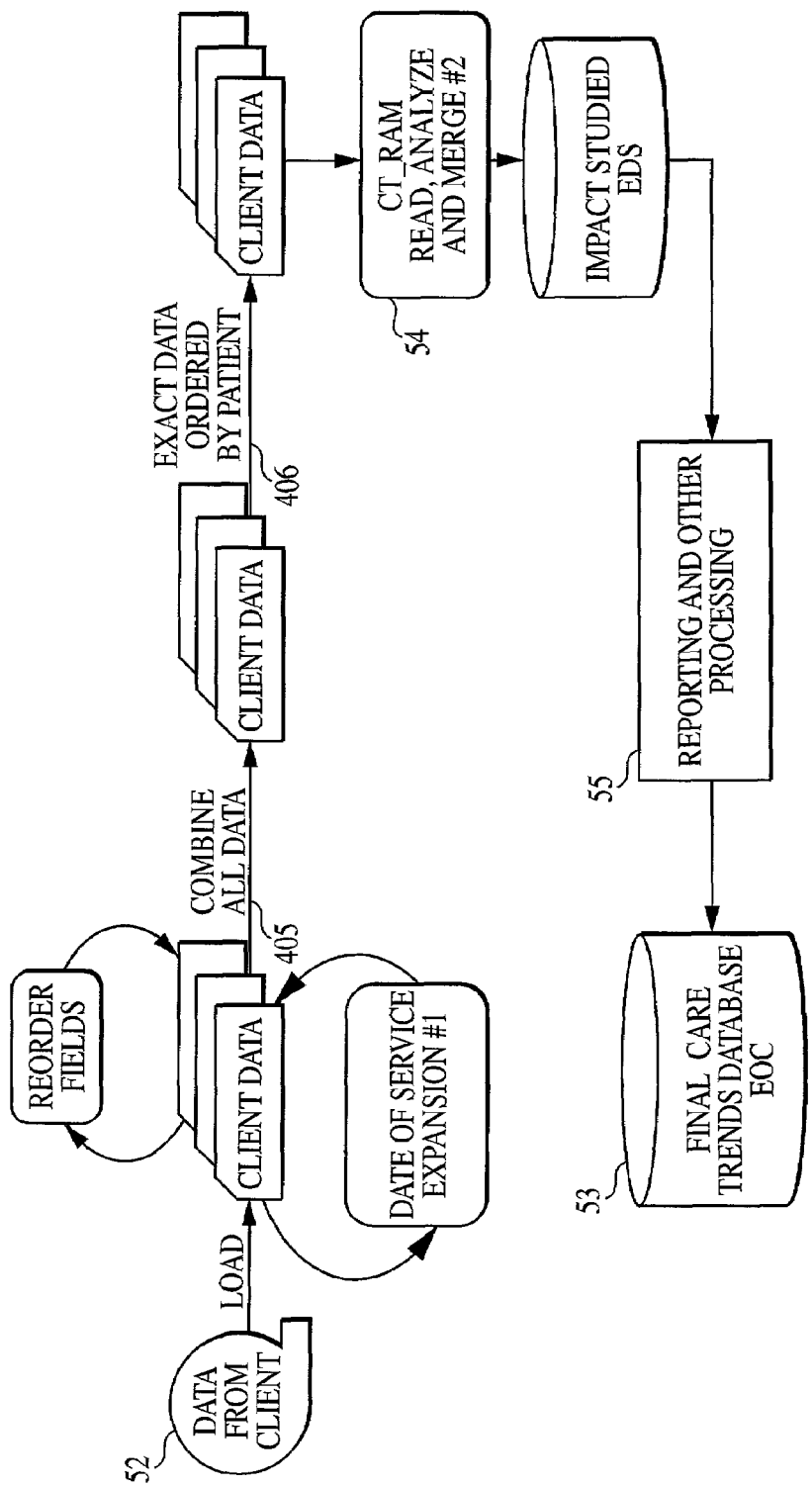
FIG. 7 is a prior art flow chart indicating how information is obtained from a client combined with existing client data, analyzed and merged with other data, and processed to determine final care trends.
Figure 8:
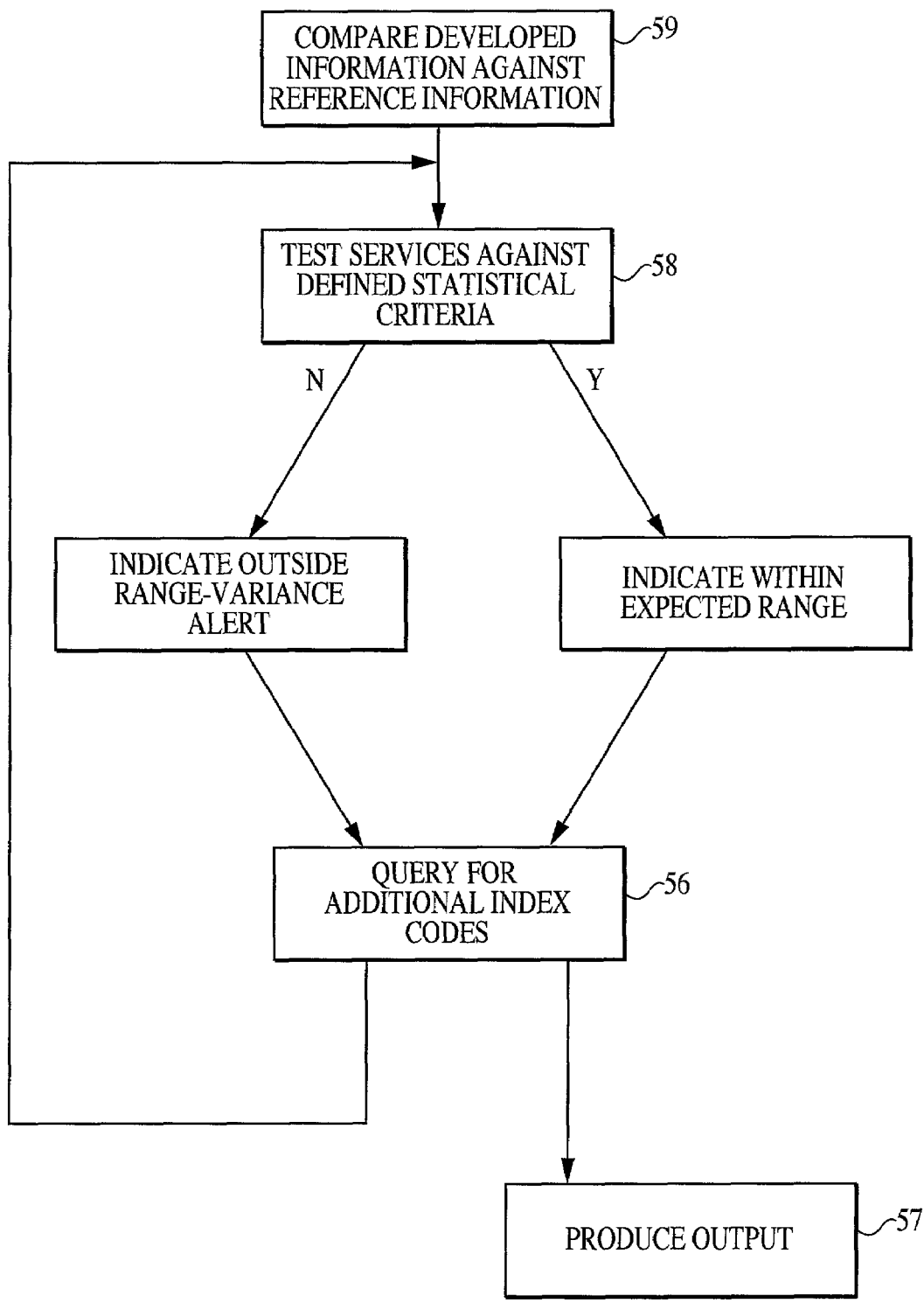
FIG. 8 is a prior art flow chart illustrating the method of comparing profiles, testing services against statistical criteria, and producing an output of these comparisons.
Figure 9:
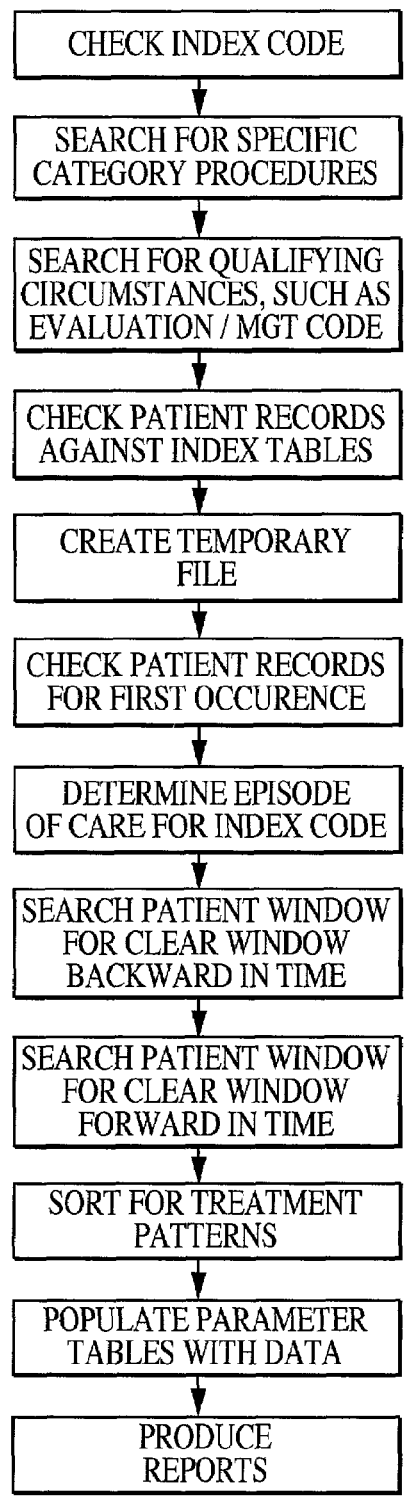
FIG. 9 is a prior art flow chart indicating how the reports are produced by search for specific category procedures, qualifying circumstances, checking patient records against index table, checking for the first occurrence, the episode of care, and sorting for treatment patterns.
Figure 10:
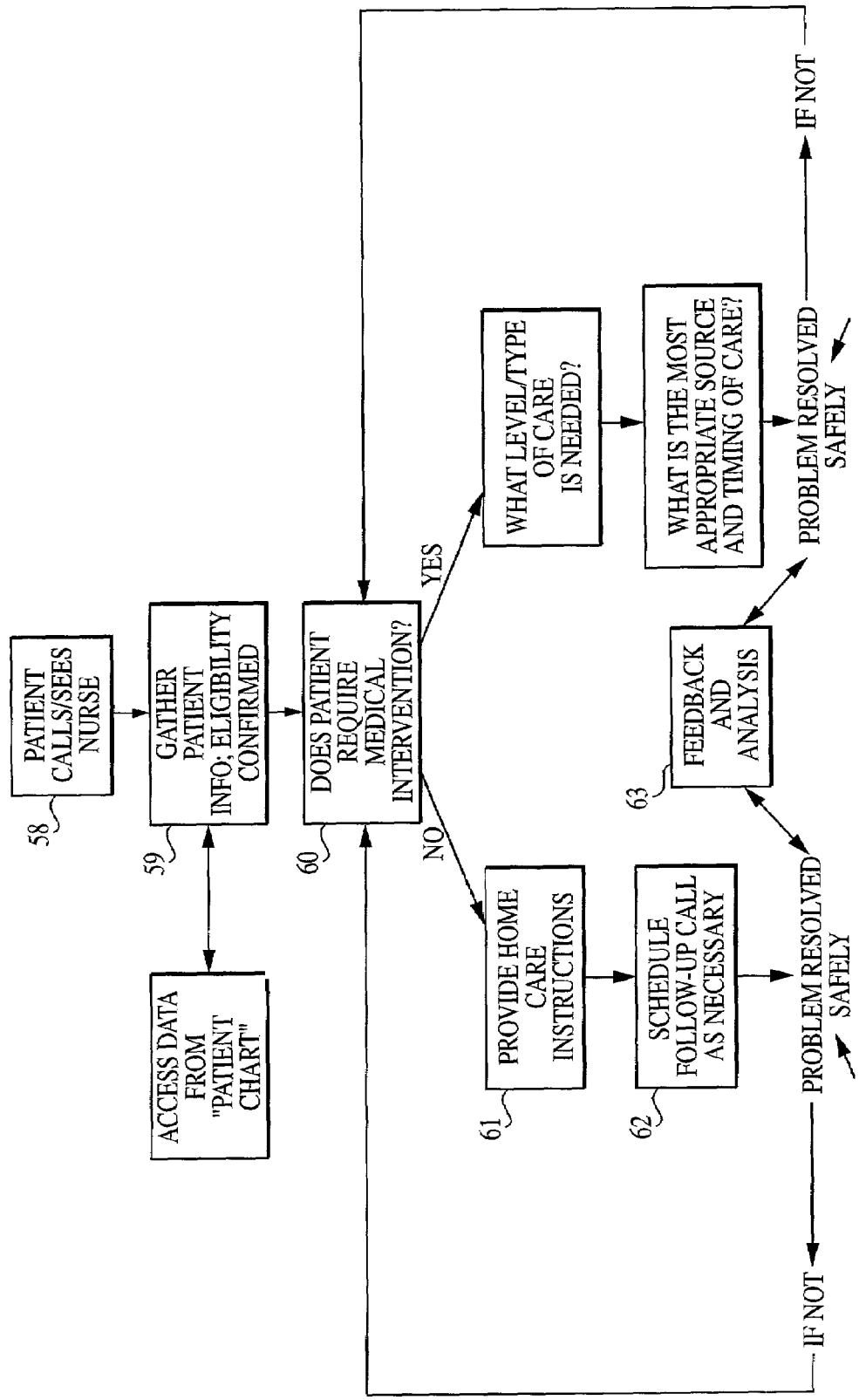
FIG. 10 is a prior art flow chart of the network management system of this prior art. It depicts how patients call in, information is gathered from the caller and a patient care chart and it is determined whether the patient needs medical intervention (for example, home care instructions)
Figure 11:
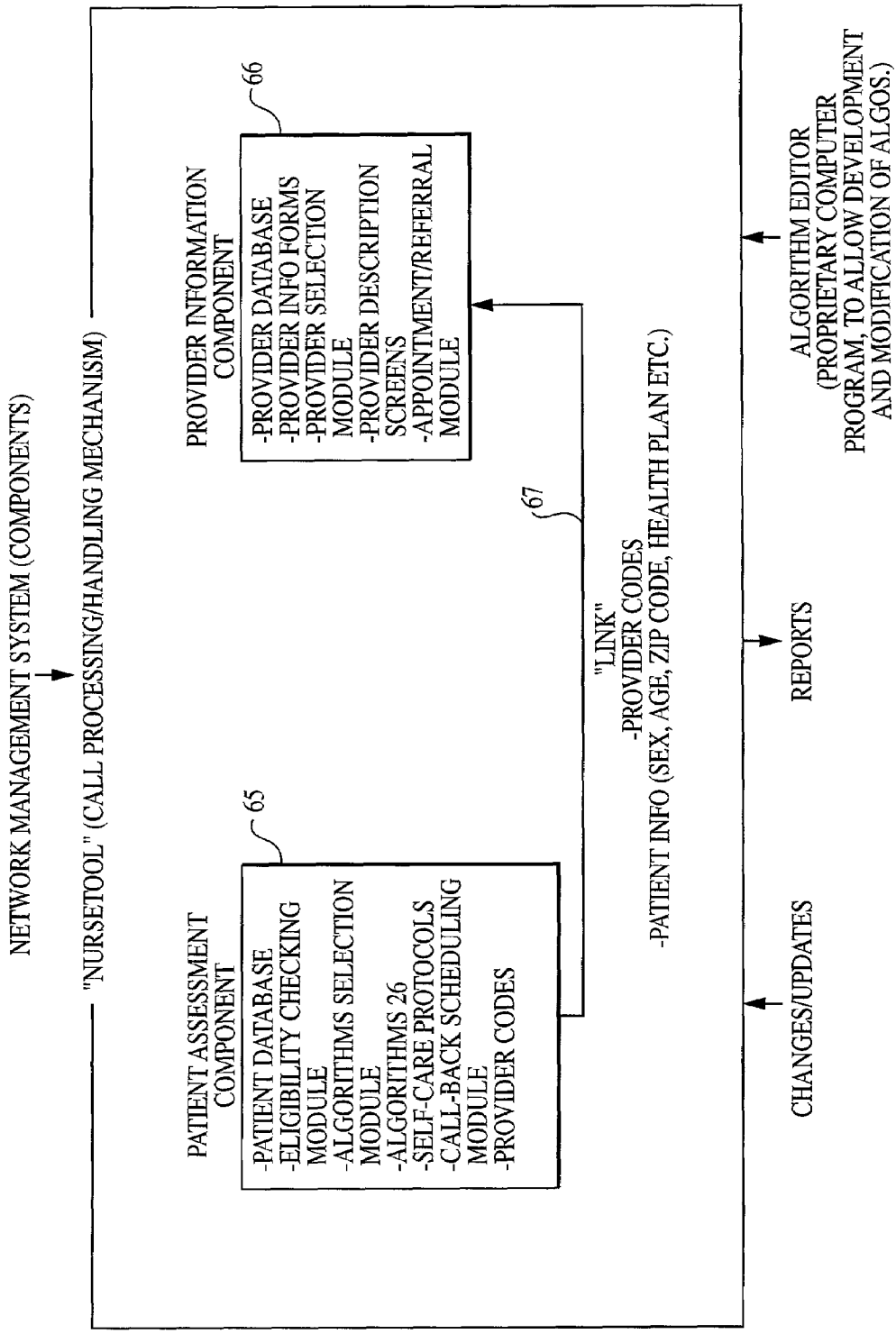
FIG. 11 is a prior art flow chart depicting the patient assessment and provider information components of the Network Management system and how these two components are linked and used to produce reports, changes and update, and used with algorithm editors programs to allow development of and modification of such algorithm.
Figure 12:
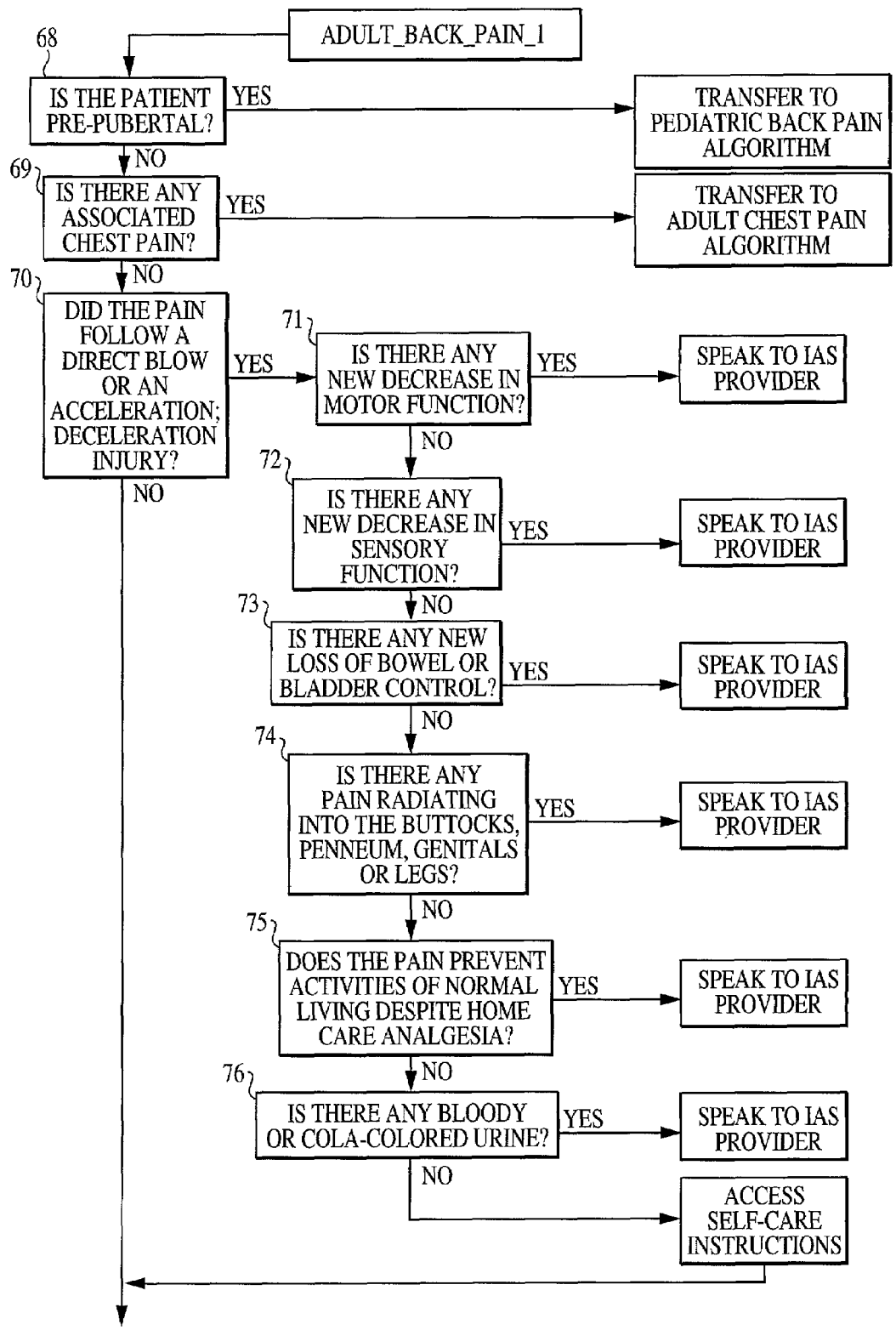
FIG. 12 is a prior art flow chart which depicts a branched change logic algorithm for assessing a patient for an appropriate timing and type of medical care.
Figure 13:
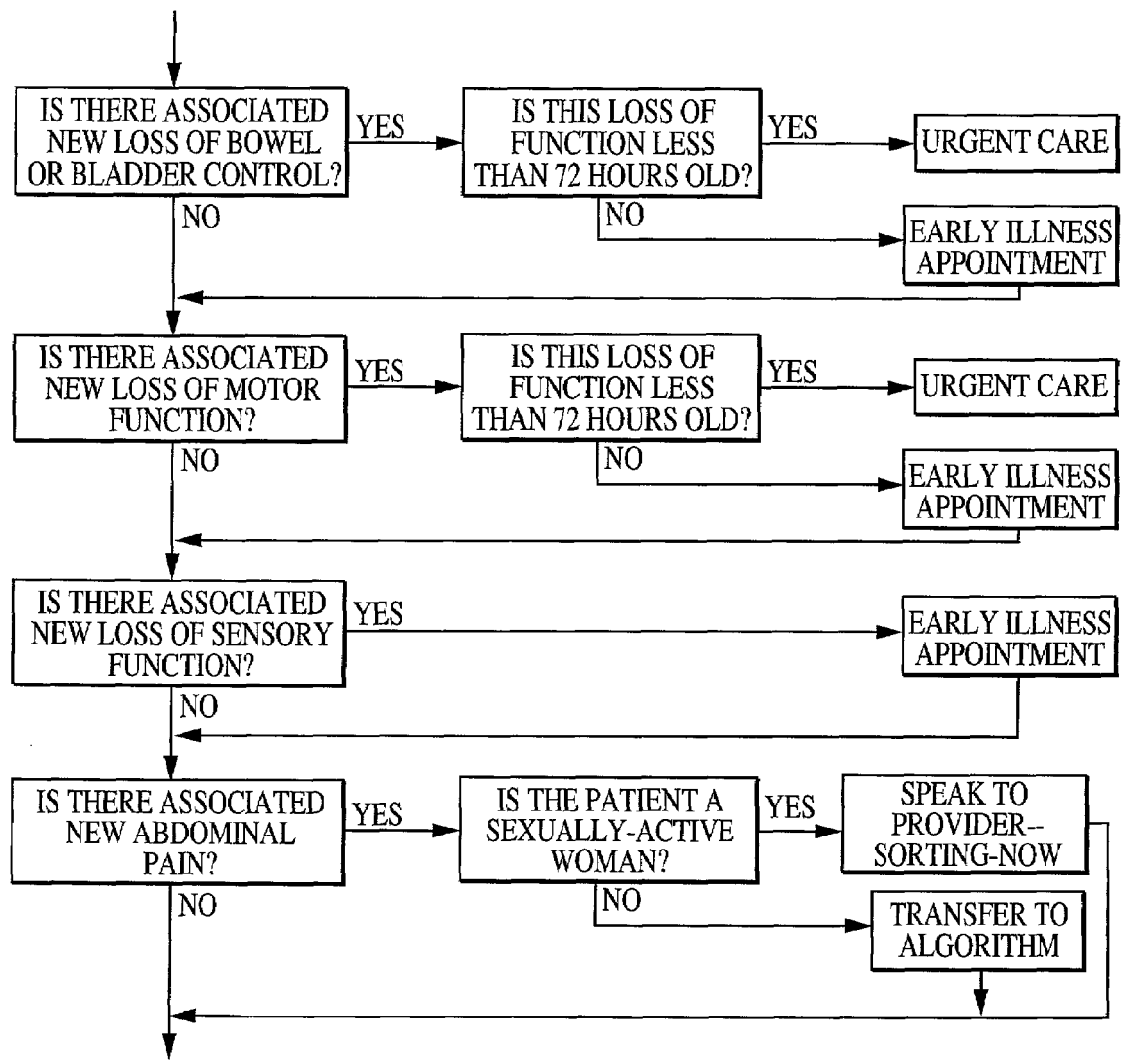
FIG. 13 is a prior art flow chart which depicts another of branched change logic algorithms for assessing a patient for an appropriate timing and type of medical care.
Figure 14:
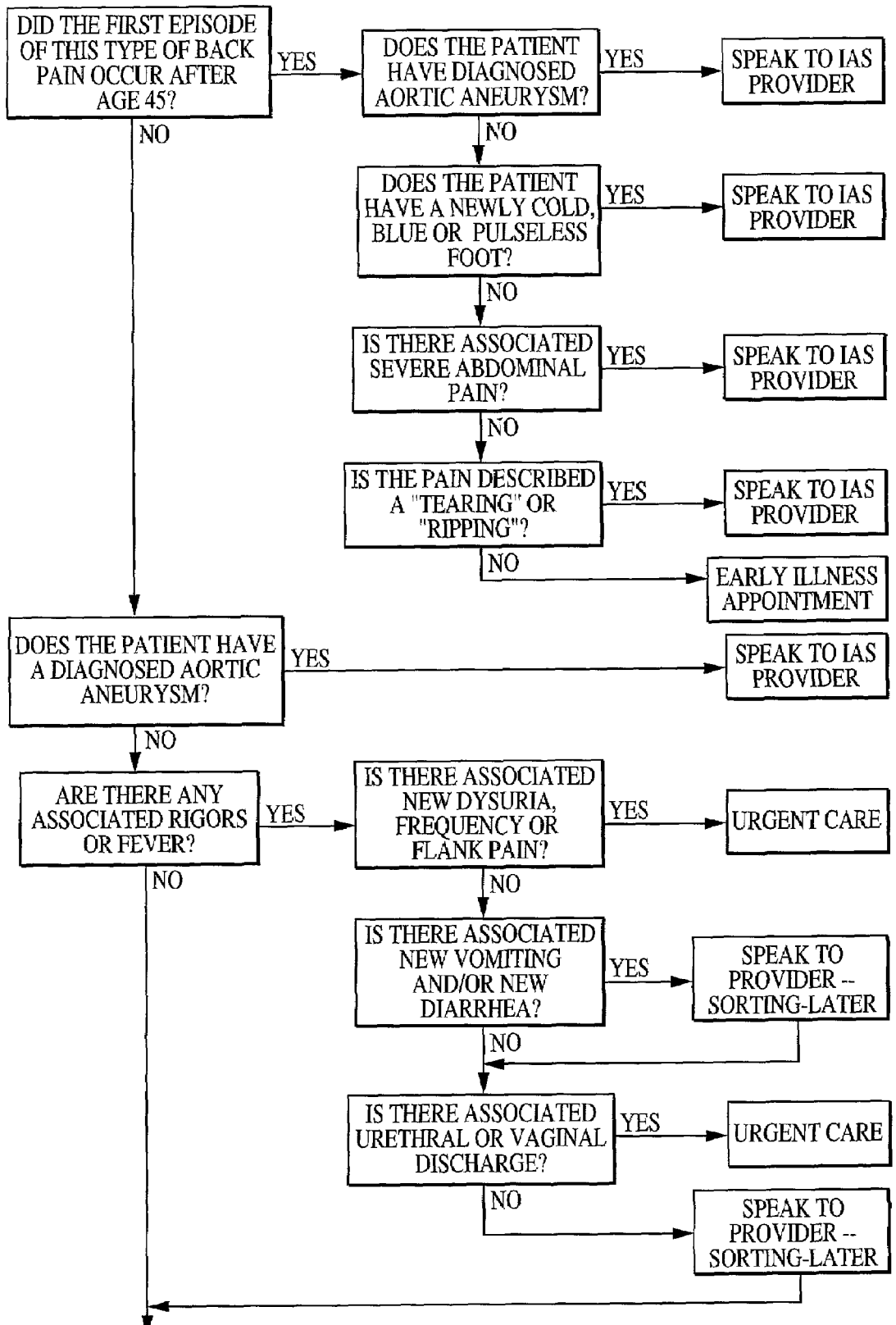
FIG. 14 is a prior art flow chart which depicts another of branched change logic algorithms for assessing a patient for an appropriate timing and type of medical care.
Figure 15:
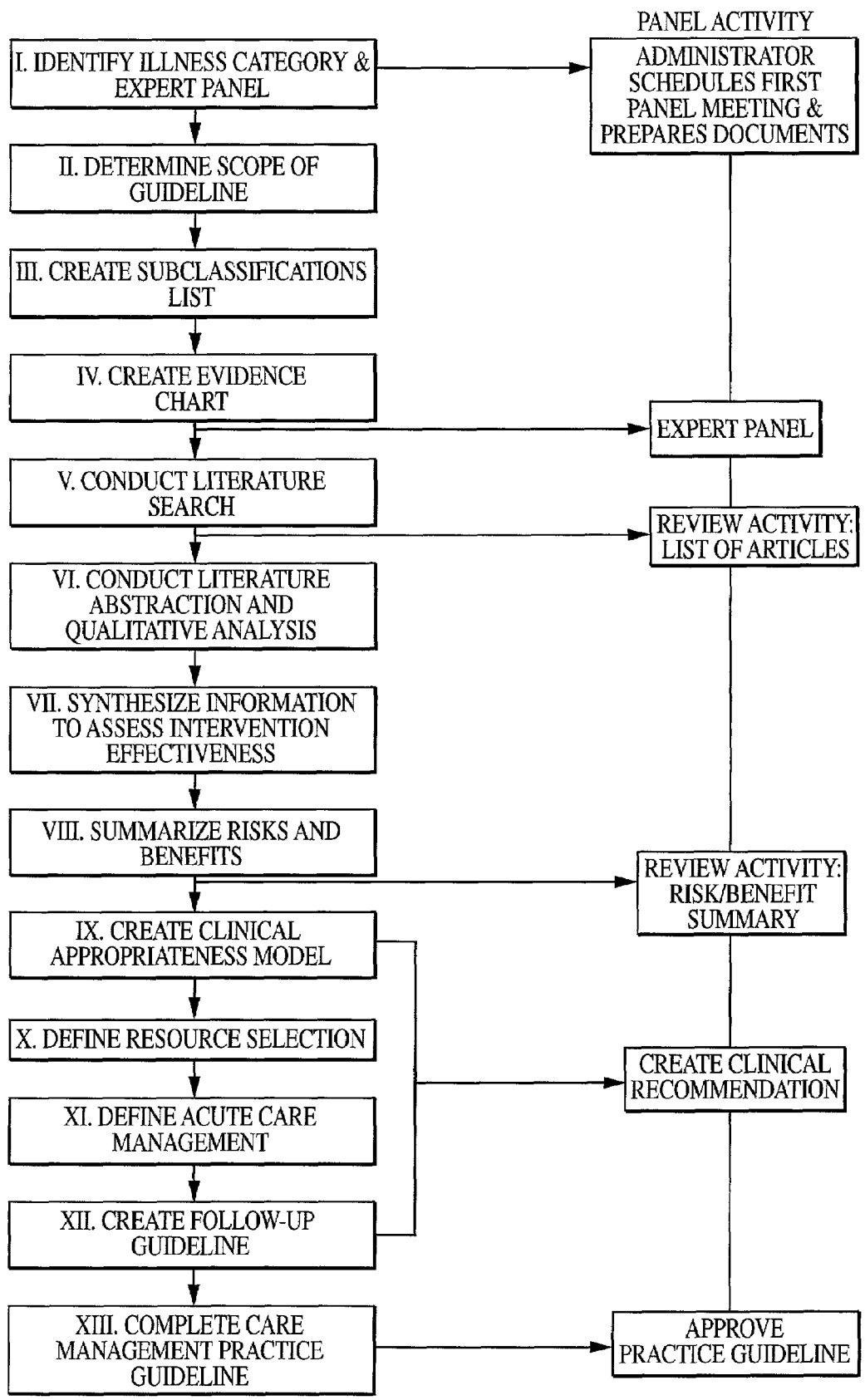
FIG. 15 is a prior art flow chart of the steps in creating a care management practice guidance from identification of the illness category and expert panel through developing a scope of the guideline, classifications, evidence charts, literature searches, summaries of the risk and benefits, and other factors.
Figure 16:
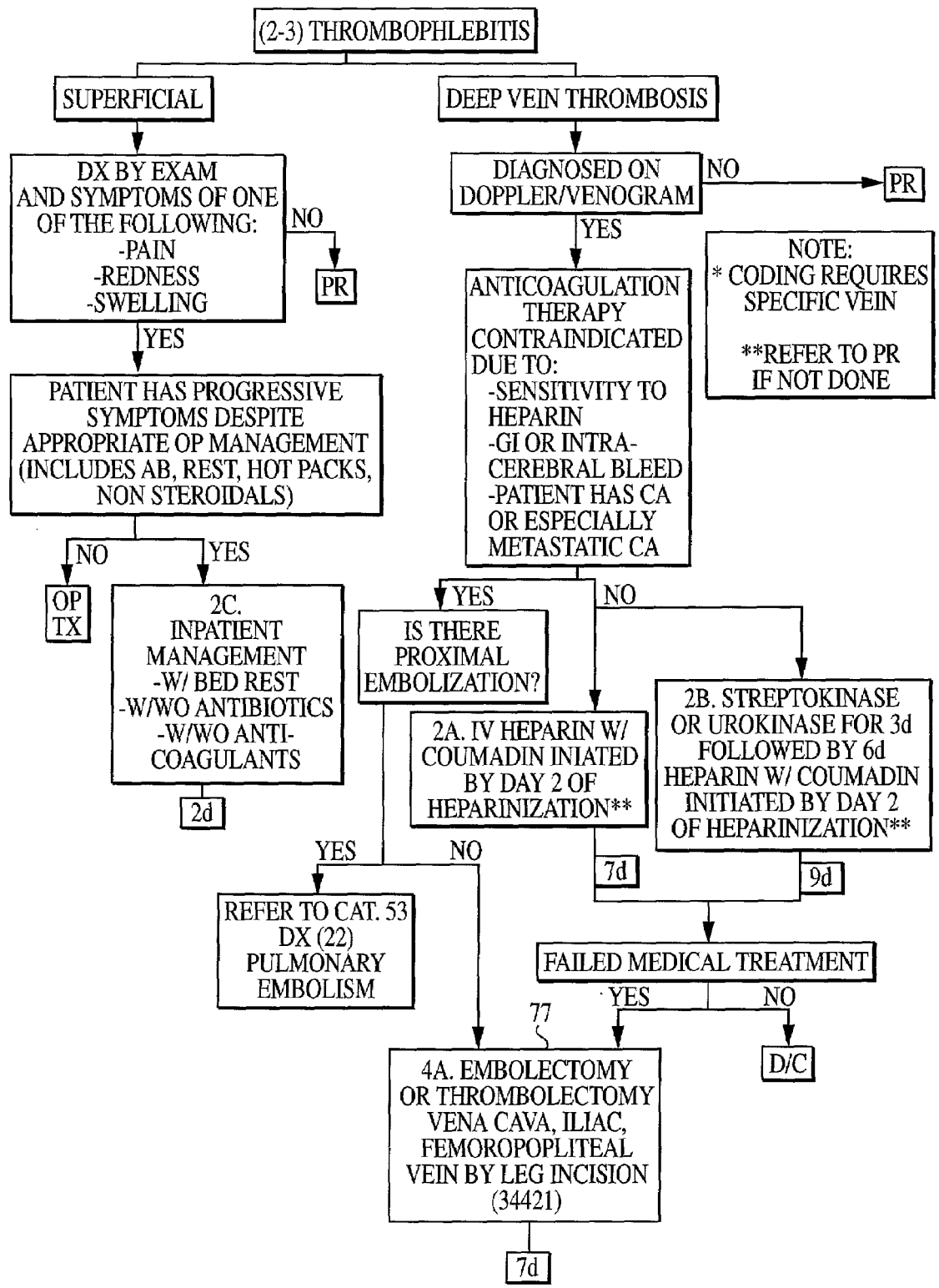
FIG. 16 is a prior art flow chart of the diagnostic decision tree used for thrombophlebitis.
Figure 17:
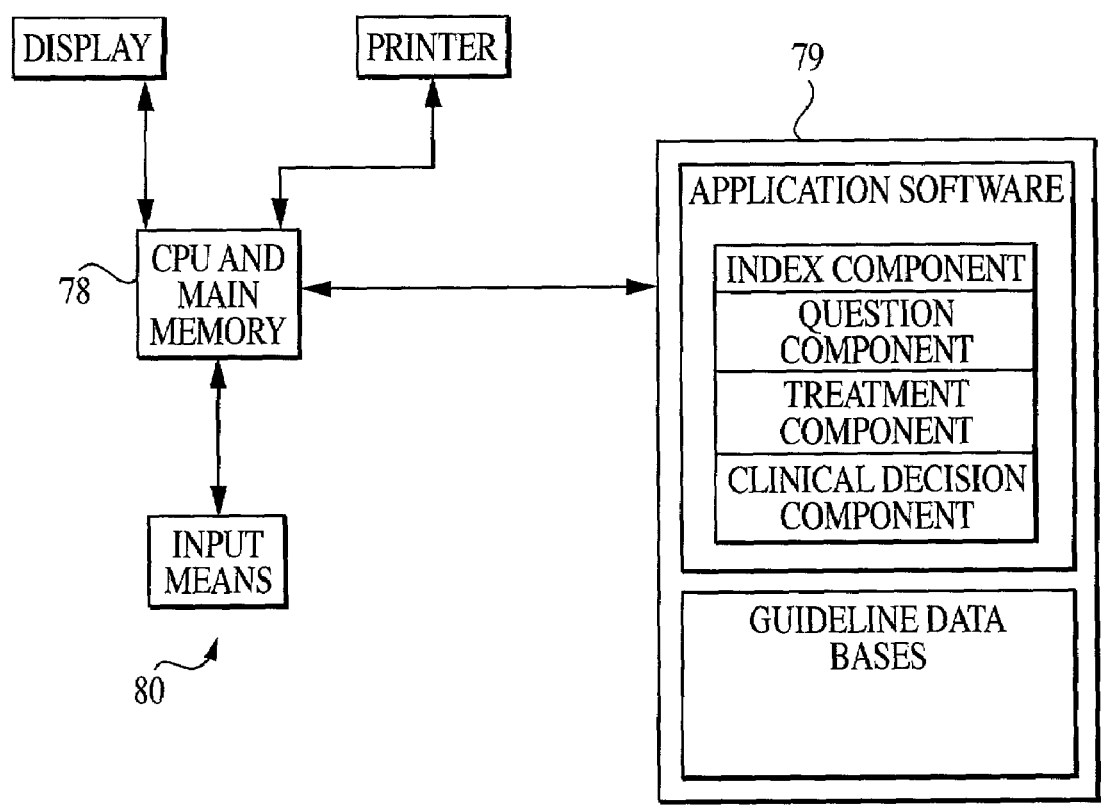
FIG. 17 is a prior art flow chart of the hardware used.

The detailed descriptions which follow may be presented in terms of program procedures executed on a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices.

The present invention also relates to apparatus for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove more convenient to construct more specialized apparatus to perform the required method steps. The required structure for a variety of these machines will appear from the description given.

DETAILED DESCRIPTION OF THE BEST MODE OF THE INVENTION

Reference now will be made in detail to the presently preferred embodiments of the invention. Such embodiments are provided by way of explanation of the invention, which is not intended to be limited thereto. In fact, those of ordinary skill in the art may appreciate upon reading the present specification and viewing the present drawings that various modifications and variations can be made.

For example, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

The Care Assessment Tool for health care management of the present invention (hereinafter Care Assessment Tool or CAT) is a computer assisted and/or implemented program designed to assess patient risk and potential eligibility to health management or other programs. The tool provides, for example, a consolidated repository of patient medical and/or lifestyle information.

The Care Assessment Tool goals are to improve or maintain patient care, while lessening the number of patient surveys and streamlining and reducing the cost associated with program development and approval by normalizing questions across programs. This patient review process ensures appropriate patient-specific care through the collection of extensive information on a patient's medical and drug utilization history, answers to core questions, diagnostic data, and patient initiated inquiries on health care issues.

For purposes of the present invention "health care condition" is broadly defined to mean a condition in the nature of a disease or an organic dysfunction or a "condition" that might also be viewed as a status or an outcome.

Advantageously, the process and/or system of the present invention is used in connection with a computerized central repository of patient information from a member profile, drug claims records, self-reported information, medical claims records, general demographic data, eligibility data, and demand for medical services. In addition, the present invention optionally includes an interactive contact (e.g., in-person, telephone, computer, and the like) between the health care plan provider and the patient as a unique component of the program.

The present invention provides a computer implemented and/or assisted process for one or more of eliminating redundant, repetitive surveying of patients with multiple medical conditions, identifying potentially high health care resource utilizers in a population, improving clinical information for use by drug utilization review, care management and prior authorization programs, and/or identifying likely candidates for other health management programs while improving or maintaining the quality of care in a patient population.

The present invention provides a computer implemented and/or assisted process for creating a central comprehensive information profile on the health of the patient utilizing, among other sources of information, existing medical claims and drug claim files and the interactive selection and/or collection of extensive information on a patient's current medical condition, demographics, and behavior. The present invention also assists, optionally in real-time, the identification of potential drug-disease and drug-drug adverse affects. By combining diagnoses information, vital statistic information and drug claim related information from a variety of internal and external sources/databases, the present invention provides the ability to provide the highest quality care.

The review program of the present invention is designed to gather information on the health status of the existing patient and the preventive programs for which the patient is qualified. The benefits of the present invention include significantly improving or maintaining patient care and increasing the quality of care through more personalized, meaningful health education messaging, while controlling or reducing the cost of patient care.

Figure 20:
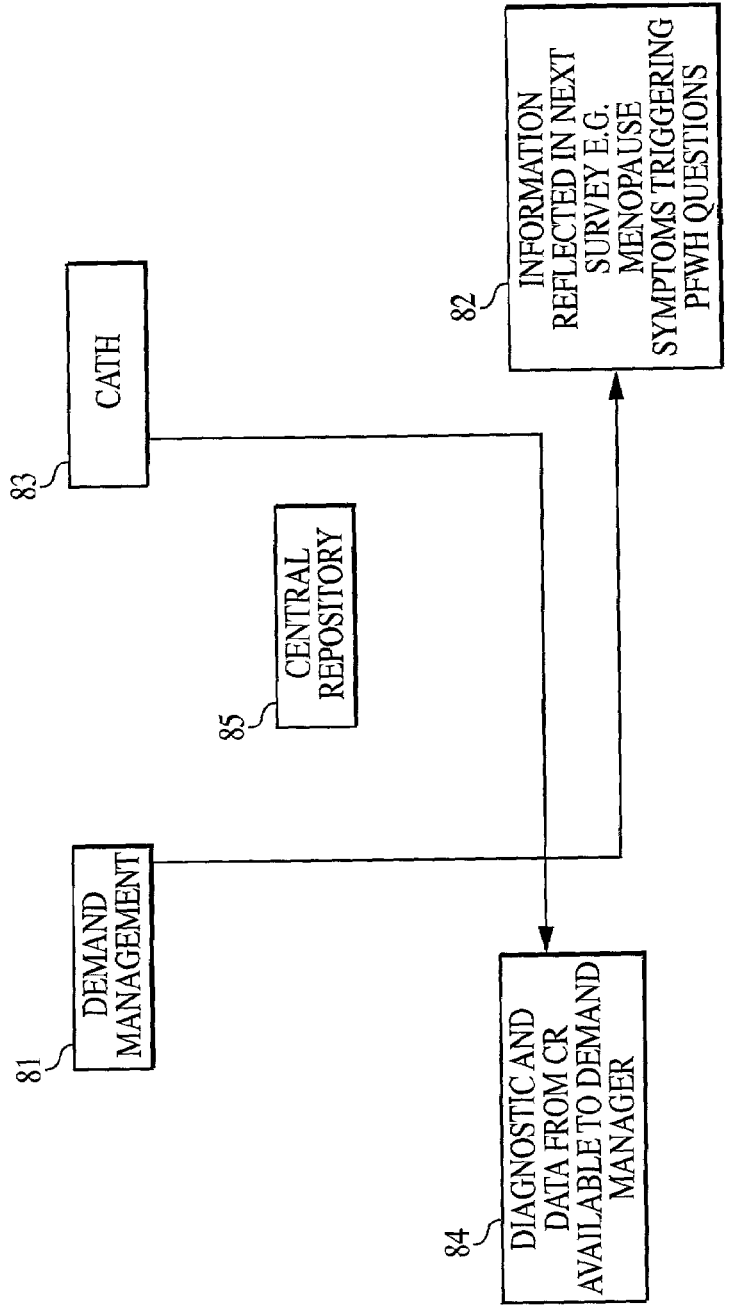
FIG. 20 of the present invention is a flow chart depicting the overall link between Demand Management, the Care Assessment Tool for health care management, the Central Repository, the diagnostic data, and the data gathered from the interactive survey performed as part of this invention.

A unique feature of the present invention is its ability to be utilized in demand management 81 (FIG. 20) and care assessment 83 aspects of the health care process. The central repository 85, in effect, links and provides a central source of data from diagnostic sources 84, patient initiated inquiries, information selected by provider, and information obtained from periodic surveys 82.

Figure 21A:
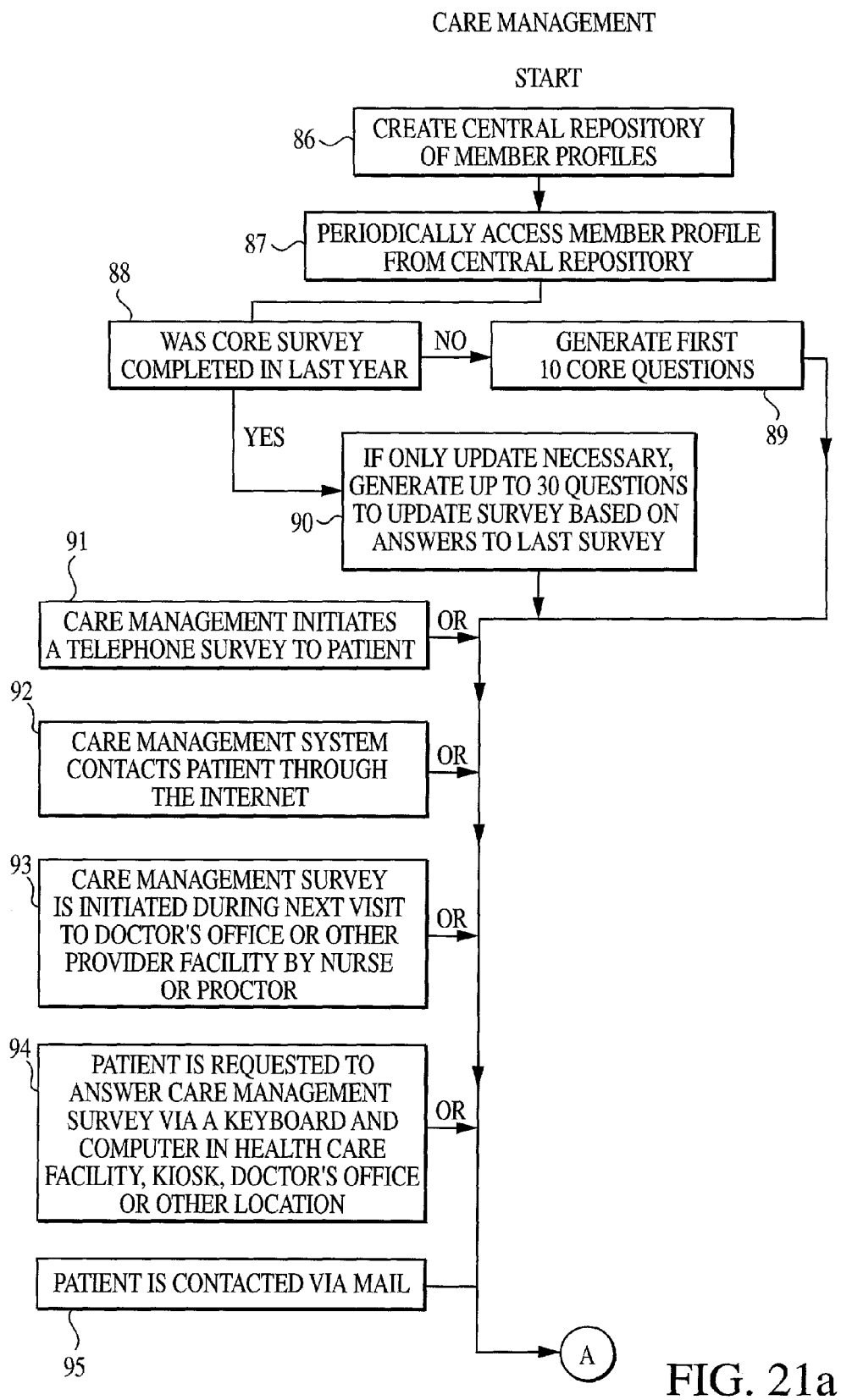
FIGS. 21a and 21b are a generic block diagram illustrating the components of the preferred embodiment of the computerized Care Assessment Tool system of the present invention. The figure illustrates the embodiment, for example, using a telephone survey, an internet connection, live interviews, computer interactive response in a health care facility, and the mail.

One mode of the invention is the care assessment tool (see FIG. 21a), although the invention can be used in various aspects of the health care system. In the initial step, a central repository of patient profiles is created for each member of the plan 86 (FIG. 21a). In the care management mode, initially at the beginning of the program and periodically thereafter, the member profiles in the central repository are accessed to determine if the member's profile has been updated with an interactive survey within the last year 87.

If the core survey has never been administered or at least not administered within the last year, the survey proctor determines a series of, for example, ten (10) core questions for that individual 89. If the survey core questions have been administered within the last year, the survey proctor determines a series of, for example, up to 30 follow up questions 90. The specific core and follow up questions are determined based on a set of rules for determining the specific questions (see Appendix A, a list of exemplary core question and Appendix B which lists exemplaries of the key 40 questions and the decision criteria and attributes used in the core survey expert system). The core survey expert system 89 which includes the potential questions, the rules for determining which questions are asked, and other factors is discussed in more detail below.

The proctor or other health care personnel then initiates an interactive survey of the patient. This survey can be initiated, for example, by a telephone survey 91, an Internet inquiry 92, a live interview in a doctor's office or other location 93, contact through the use of a touch screen or computer key pad in a kiosk, doctor's office or other location 94 or through a mailed response from a written initial survey mailed to the patient 95 (FIG. 21a). The response time and mechanics of obtaining the answers to the survey will differ slightly based on the type of method that is used to contact the patient.

Other rules and/or core questions may also be used in the present invention that effectuate the invention's features and/or goals.

Figure 22:
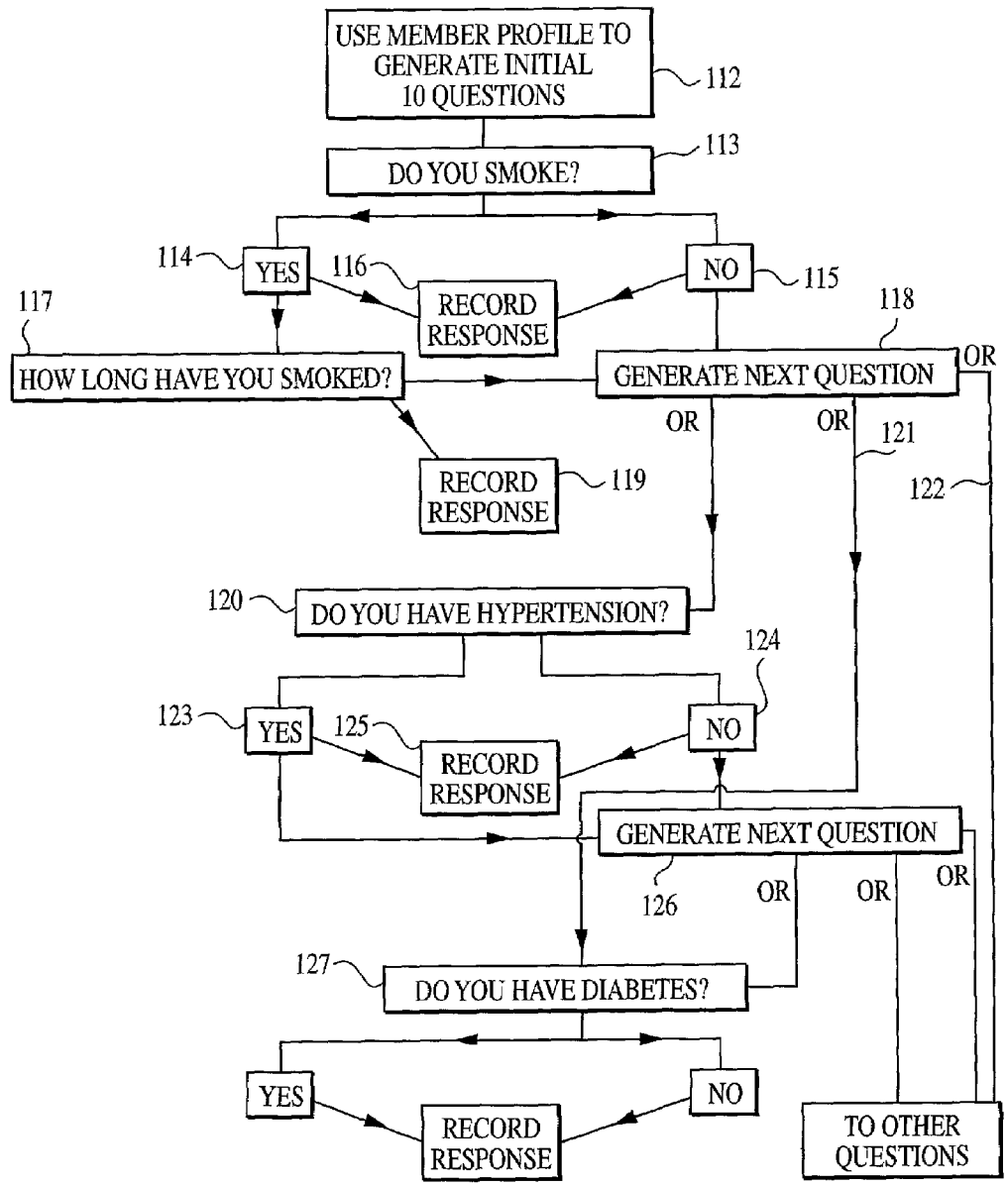
FIG. 22 is a block diagram illustrating an exemplar of the interactive core survey process.

In the present invention, the core survey questions are interactively modified and priority of questions reordered based on answers to the questions. FIG. 22 illustrates an exemplar of an interactive modification of the priority question. For example, the member profile is accessed to generate the initial list of questions 112. The member is asked if he or she smokes 113. If the answer is yes 114, the answer is recorded 116 and the member is asked for how long have they smoked? 117. If the answer is no 115, the answer is recorded 116 and another question is generated 118. Depending upon the member profile information and whether the member smoked, the next question may be Do you have hypertension? 120, or Do you have diabetes? 127 or some other question 122. In each case, the yes 123 or no 124 answer is recorded 125 and another new question generated 126. Advantageously, in the present invention, the system intelligently determines the questions that are needed to be responded to, for example, via use of drug markers. For example, in the situation of diabetes, if the member indiates that they are taking insulin, there is no need to ask whether they are diabetic.

In response to inputting the response to each prior question 116, the core survey expert system: (1) informs the survey giver of the specific follow up question to ask; (2) raises or lowers the priority for asking other questions; (3) determines when certain questions are completely suppressed; (4) determines whether and how to validate the information obtained; and/or (5) provides specific instructions on how to classify and process the information 118 (FIG. 22).

Iteratively after each response is entered into the system 116 (FIG. 22), the expert system: (1) prioritizes the specific follow up questions; (2) raises or lowers the priority for asking other questions; (3) determines when certain questions are completely suppressed; (4) determines whether and how to validate the information obtained; and/or (5) provides specific instructions on how to classify and process the information. Since this invention involves an iterative, interactive process, the actual questions asked during this 30 question sequence 99 (FIG. 21b) depend upon the answers to the prior questions. For example, if the patient has already been surveyed, the survey proctor optionally starts with a list of up to 30 questions generated by the expert system prior to the call 90 (FIG. 21a).

When the survey was not performed within the last year 98 (FIG. 21b), after the answers to the first ten questions are recorded 96, another set of questions, for example 30 questions, are generated 99, asked 96, and recorded 97. When all of the questions have been answered, the answers are converted to computerized information 100. Additionally, the proctor answers any questions raised by the patient, if any 101.

Figure 21B:
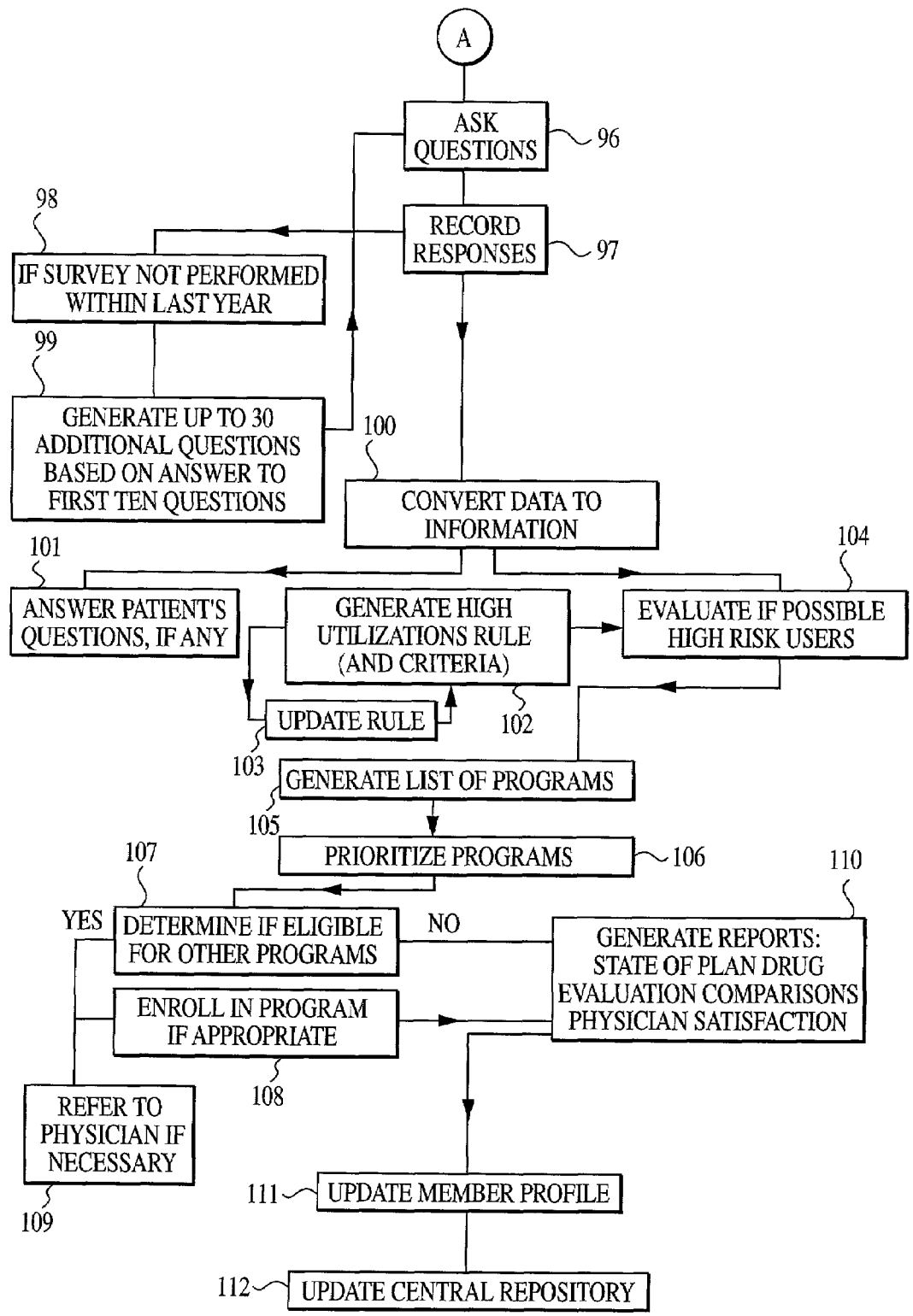

In the following step 102, advantageously existing and/or collected information is assessed to determine which medical conditions, patient characteristics or other demographic characteristics or conditions are predictive of high utilization of health care services using standard techniques and to specify the rules and decision criteria via, for example, standard medical guidelines used in the expert system for determining when a patient may be a high utilizer of health care. This information is periodically updated 103 (FIG. 21b).

In the next step of the preferred embodiment 104, the survey proctor uses the expert system to evaluate interactively if a patient is a potential high risk user. This expert system is utilized to assess whether there are intervention programs, for example, standard intervention programs, which could minimize health risks which are likely to cause high utilization of health care by the individual 105. These intervention programs are prioritized 106.

In step 107, it is determined if the patient is eligible for such intervention programs utilizing the expert system and, based on predetermined criteria, such as age, medical condition, and the like. Then, the patient is enrolled in any appropriate new program if he or she is willing 108.

In the next step of the preferred embodiment 109, if the patient asks specific medical and/or health questions, either the questions are answered, the patient is referred to his or her doctor, or the patient is referred to a standard health management program.

In step 110 of the preferred embodiment, the health care provider specialists generates reports using the central depository and the computer assisted expert system, concerning, among other things: (1) the state of plan; (2) drug evaluation; (3) comparisons, if appropriate; (4) updating the patient profiles; (5) updating the entire central repository.

Finally, the patient profiles 111 and central repository 112 are updated based on the information gathered. The central repository 112 is periodically reviewed to select patients who have not had the survey performed or who need to have their survey updated.

Patient Profile and Central Repository

Figure 23:
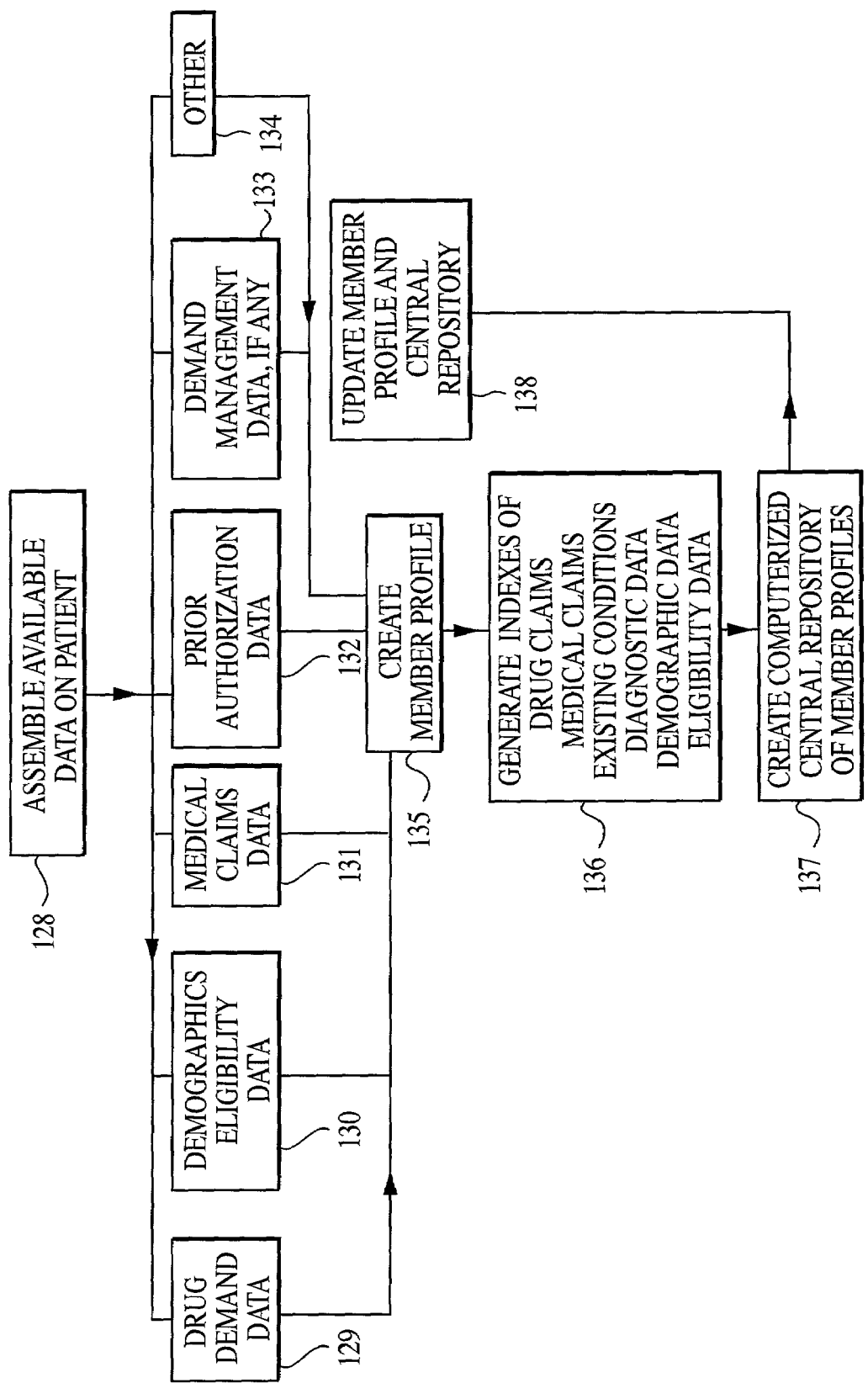

The patient profiles 135 are created (FIG. 23) by assembling from available data 128 existing drug claims data 129, demographic data 130, existing medical claims data 131, prior authorization data 132, demand management files 133, other external sources 134 and/or self-reported lifestyle and behavioral information. From these member profiles, an index of drug claims, medical claims, demographic data, and eligibility data is generated 136. Thus, advantageously, this invention collects information from existing separate program files, including, but not limited to, demographic information, health care program availability and eligibility criteria, current health care participation information, individual medical claims, individual drug claims, prior medical history, prior drug usage patterns (including nonprescription drug usage), known behavioral factors (e.g., smoking), and information obtained through a demand management program (such as the Nurse Triage Program), if available. The demographic data may be only patient identification, age, gender, and geographic location or it may include additional information.

The next step 137 involves advantageously combining into a master central repository all of the individual, member health profile information 135.

Core Survey Expert System Component of the Invention

Figure 24:
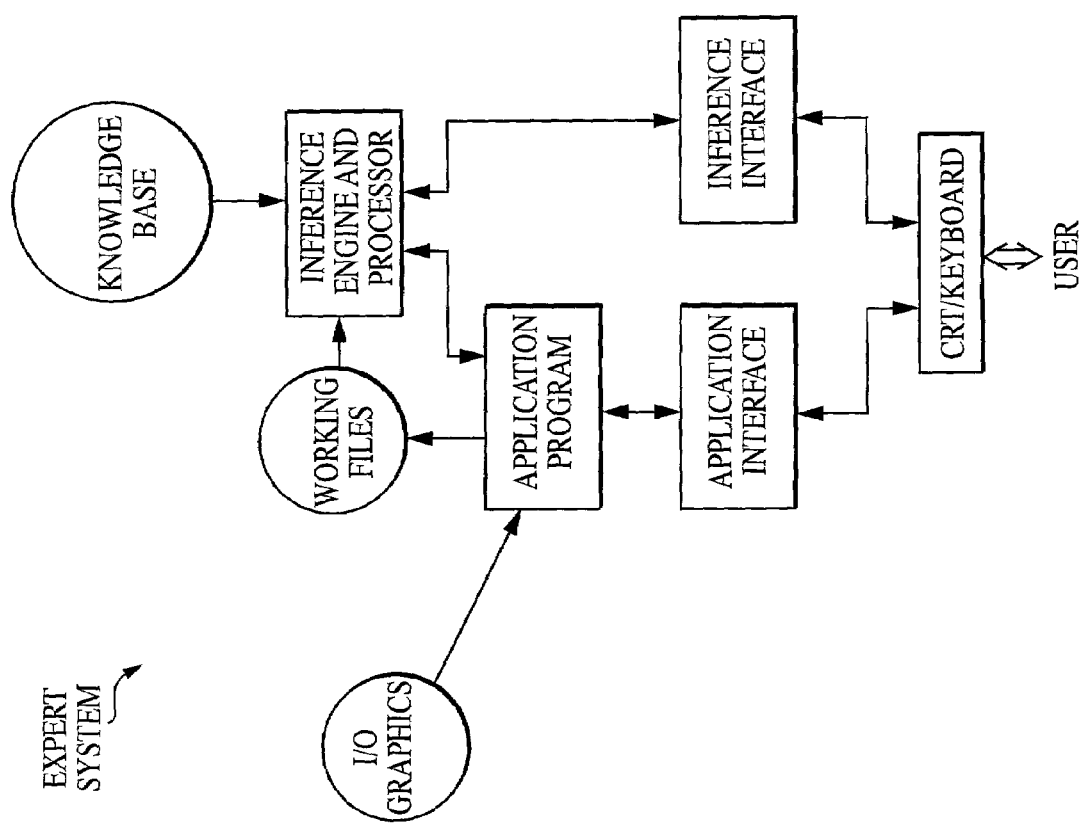
Figure 25:
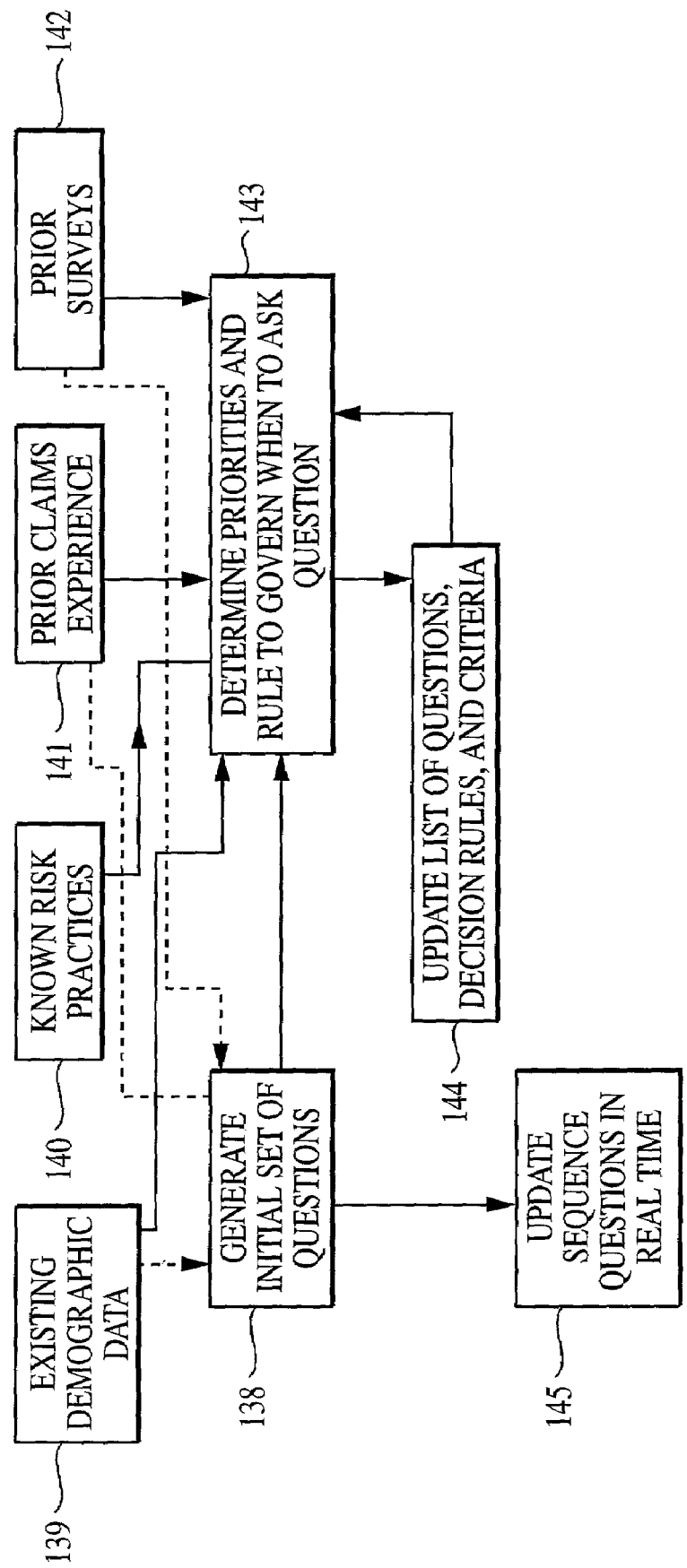
FIG. 25 lists the steps used to generate and update the core survey questions used in the expert system of this invention.

A unique feature of this invention is the use of smart or predetermined heuristic rules via an expert system (FIG. 24 a general description of an expert system) to perform the interactive survey of patients, to identify potential high utilizers of health care, and to identify and enroll patients in other health programs which are likely to address their health care needs proactively. This component ("Core Survey Expert System") is common to all embodiments of the invention. FIG. 25 lists the steps used to generate and update the core survey questions used in the expert system of this invention.

In the initial step of the core survey expert system (see FIG. 25), a list of core survey questions 138 is developed prior to any contact with the patient, based on demographic data 139, risk factors 140, prior claims experience 141, and information obtained from the patient in prior surveys 142. The survey questions request information on general health status, current medical treatment, high risk behavior, medical conditions, and other relevant information (FIG. 26). These core questions (those which may be utilized in the first ten sequence of questions and others for use as follow up questions) are provided in Appendix A and in Appendix C (which also includes the decision rules and other information relevant to the invention).

In step 143 of the core survey expert system (see FIG. 25), a set of priorities and rules governing when to ask each question is generated from the same sources. These rules and priorities are a central component or important aspect of the invention. Appendix C lists the exemplary rules for the core survey, and Appendix B lists the exemplary rules to determine what drug markers need to be pulled for each health management program. These table-based rules are included in the database when core survey results are stored.

Appendix D provides a more detailed description of the potential health condition questions, and the rules concerning what information triggers which questions. The potential health condition questions include, for example, questions concerning how the patient feels, whether there have been weight losses or gains, what risk factors the patient exhibits (such as smoking), whether there are any key medical conditions (such as hypertension), what is the current and past prescription and nonprescription drug use, and other similar factors (FIG. 26).

In implementing the core survey expert system, the survey proctor selects a particular set of initial ten core survey questions 89 (FIG. 21*a*), depending upon the demographic and other information available on the patient from his Patient Profile in the Central Repository (see Appendix A). If a survey has never been completed, an initial list of 10 core questions is generated. The remaining 30 questions are generated in an interactive manner 90. The precise initial ten core questions and the, for example, up to 30 additional questions are determined interactively based on the patient's profile and the response to each preceding question. The patient profile is updated advantageously in real time 111 (FIG. 21*b*).

Of course, any number of initial/preliminary and/or follow up questions may be asked. However, we have determined that it is particularly useful to use a smaller number of questions as preliminary questions to determine whether follow-up questions are needed or appropriate.

In the next step, the list of questions and the rules governing the priorities and other factors are updated from time to time based on experience with the system 143.

It is emphasized that the invention includes or contemplates revisions to these core survey questions 145 and the priorities for asking questions and rules governing when to ask a question 143. Also, additions to these questions which may be developed for other embodiments of the invention and which may be developed as more experience with the core survey expert system is obtained. These modifications are within the overall scope of this invention.

Expert System to Identify High Utilizers of Health Care

It is a unique feature of this invention to identify high utilizers of health care based on an evaluation of information in a patient profile, updated by the core survey expert system. The high utilizer recognition expert system works as follows.

In Step 146 of the high utilizer recognition expert system (see FIG. 27), information is gathered on utilization of health care and initial set of decision rules and criteria are provided 147. This list of decision rules may be standard rules from existing statistical information on which medical conditions, patient characteristics or other demographic information are predictive of high utilization of health care services is gathered.

In the next step of the high utilizer recognition expert system 148, initially after creation of the central repository, the expert system revises the rules for determining when a patient may be a high utilizer of health care based on information from the Central Repository.

Periodically, the high utilizer recognition expert system is updated 149.

ANOTHER EMBODIMENT OF THE INVENTION

Demand Management

Figure 28A:
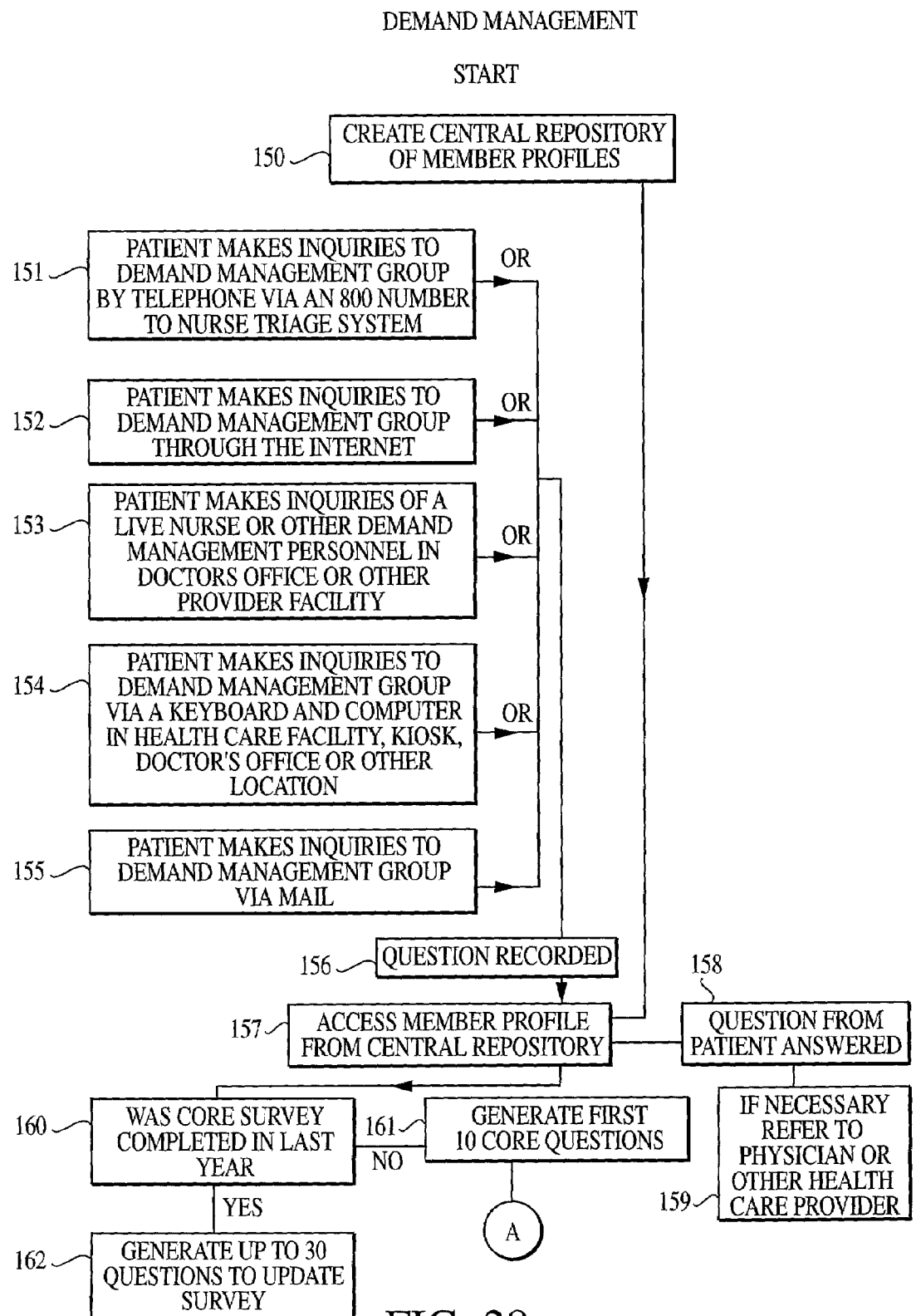
FIGS. 28a and 28b are a block diagram illustrating the second embodiment (the Demand Care) of the computerized Care Assessment Tool system of the present invention. The figure illustrates the embodiment, for example, using a telephone survey, an internet connection, live interviews, computer interactive response in a health care facility, and the mail.

A central repository of patient profiles is created 150 (FIG. 28*a*) and core questions are generated 161, as in steps 86 and 89 of one mode of the invention (FIG. 21*a*).

The core survey is performed, for example, when the patient contacts the demand management group through a telephone call to a Nurse Triage Program 151, through inquires on the internet 152, from live inquiries to a nurse or other demand care personnel in a doctors office or other provider facility 153, via keyboard or other computer in a health care facility or kiosk 154 or via the mail 155.

The person answering the telephone call or proctor/representative records the question 156 and accesses the patient's profile from central repository through the use of a computer 157. The question from the patient is answered, if possible 158. If necessary, the patient is referred to a physician or other health care provider 159.

Next, the survey proctor determines whether the core survey was completed by the patient in the last year 160. If no survey has been completed or at least not within the last year, the survey giver determines the first ten core questions 161. If a prior survey had been given within the last year, an initial list of up to, for example, 30 potential follow up questions 162 are generated, utilizing the expert system included as part of this invention (FIG. 25). Similarly, if the survey was not given within the last year and the initial ten questions have been asked 163 (FIG. 28*b*), another list of up to, for example, 30 potential follow up questions are generated 164. The survey questions request information on general health status, current medical treatment, high risk behavior, medical conditions, and other relevant information. The precise initial ten core questions and the up to 30 additional questions are determined interactively based on the patient's profile and the response to each preceding question (FIG. 22).

The patient is asked the first set of questions (for example 10 questions) (if no prior survey had occurred) 163 or asked follow up questions to update the profile if a prior survey had been administered 165. The answers are recorded 166. The core questions include, for example, the list in Appendix A. Appendix B lists the exemplary rules for the core survey.

Figure 28B:
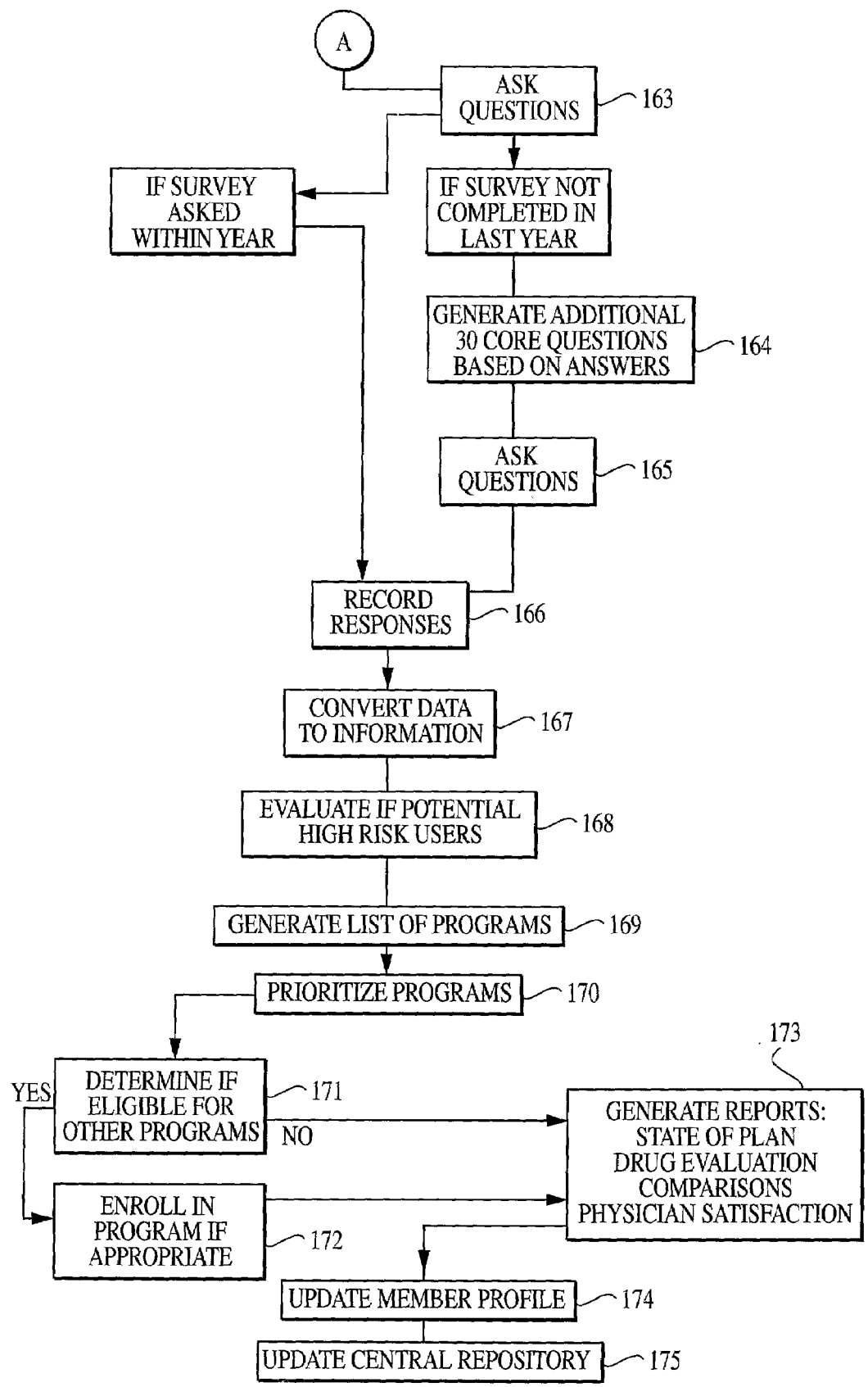

The questions are interactively modified and priority of questions reordered based on answers to the questions (FIG. 22). For example, if the patient has a medical condition, the expert system changes the list and nature of the questions based on the expert system decision rules. Next, the answers are recorded 166 (FIG. 28*b*). The data are converted into information that can be analyzed 167.

Figure 27:
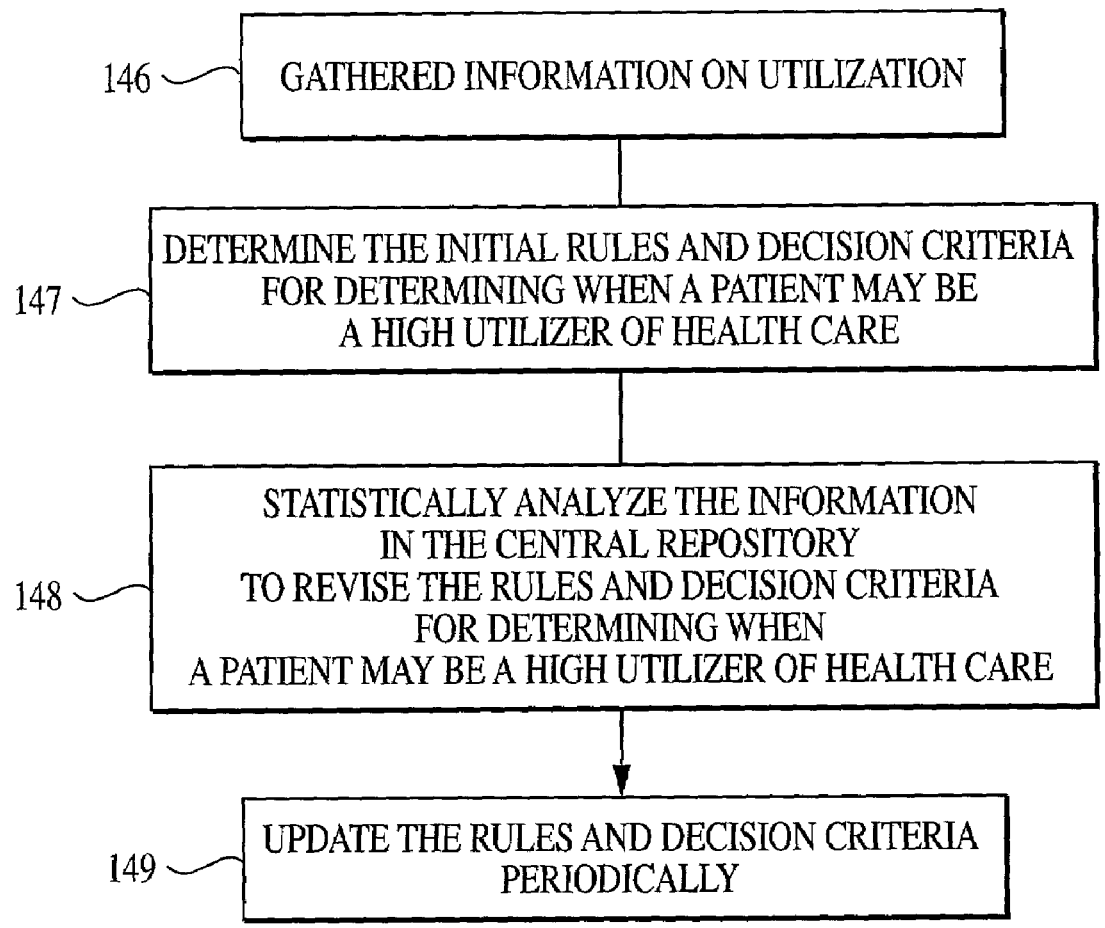

The high utilization expert system is created based on existing information in the same manner as described (FIG. 27).

The survey proctor uses the expert system to evaluate interactively if the patient is a potential high risk users 168. Next, the expert system is utilized to assess whether there are intervention programs which could minimize health risks that are likely to cause high utilization of health care by the individual 169 and each such program is prioritized 170. The survey proctor determines if the patient is eligible for such intervention programs utilizing the expert system 171. Then, the patient is enrolled in any appropriate new program upon the patient=s consent 172.

The health care provider specialist generates reports 173 using the central repository and the computer assisted expert system, concerning, among other things: (1) the state of plan; (2) drug evaluation; (3) comparisons, if appropriate; (4) update of the patient profiles; (5) update of the entire central repository.

Finally, the patient profiles 174 and central repository 175 are updated based on the information gathered.

These steps or processes can be performed by a live nurse, survey taker or other health care worker during a live interview, through a telephone interview, via the internet, via a key board and computer terminal in the doctors or other central location or via the mail.

Hardware Description

Figure 29:
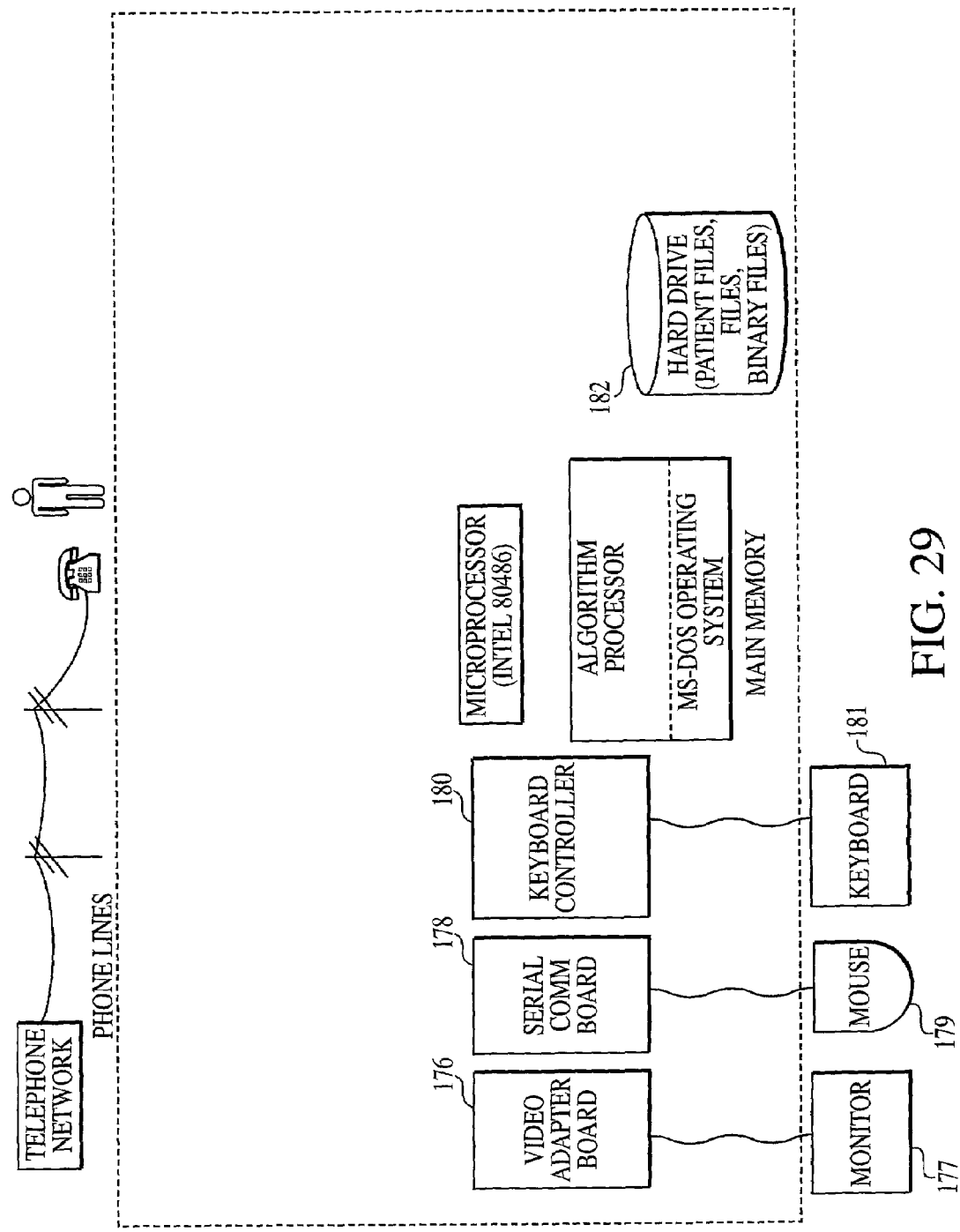
FIG. 29 is an illustration of a computer system and telephone network of a type suitable for implementing and/or assisting in the implementation of the processes described herein.
Figure 30:
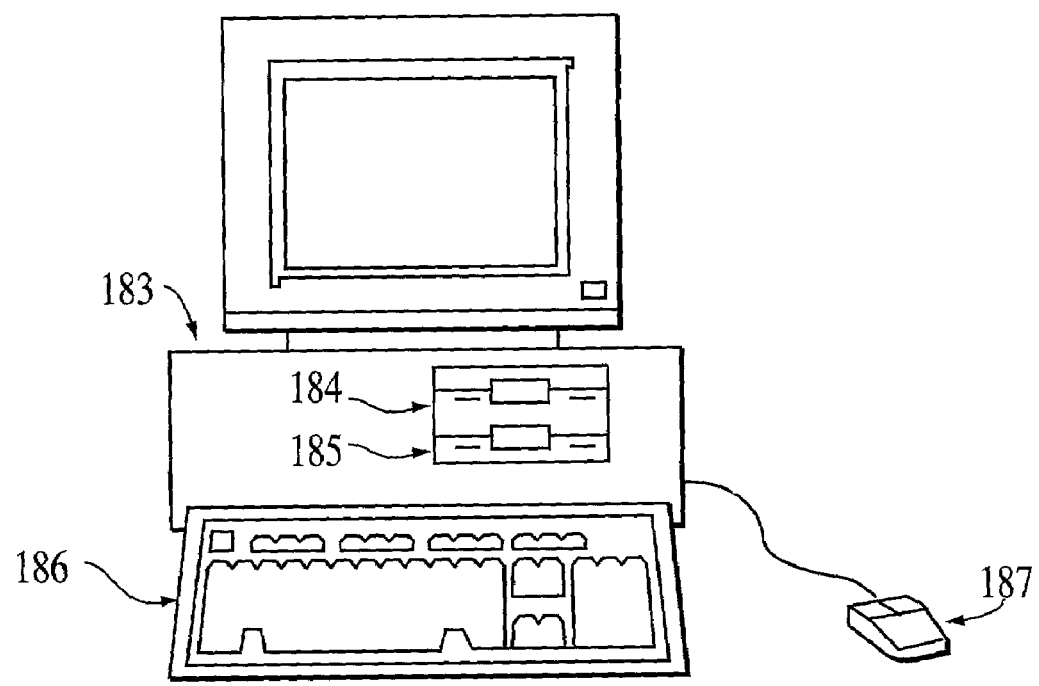
FIG. 30 is an illustration of a computer of a type suitable for implementing and/or assisting in the implementation of the processes described herein.
Figure 31:
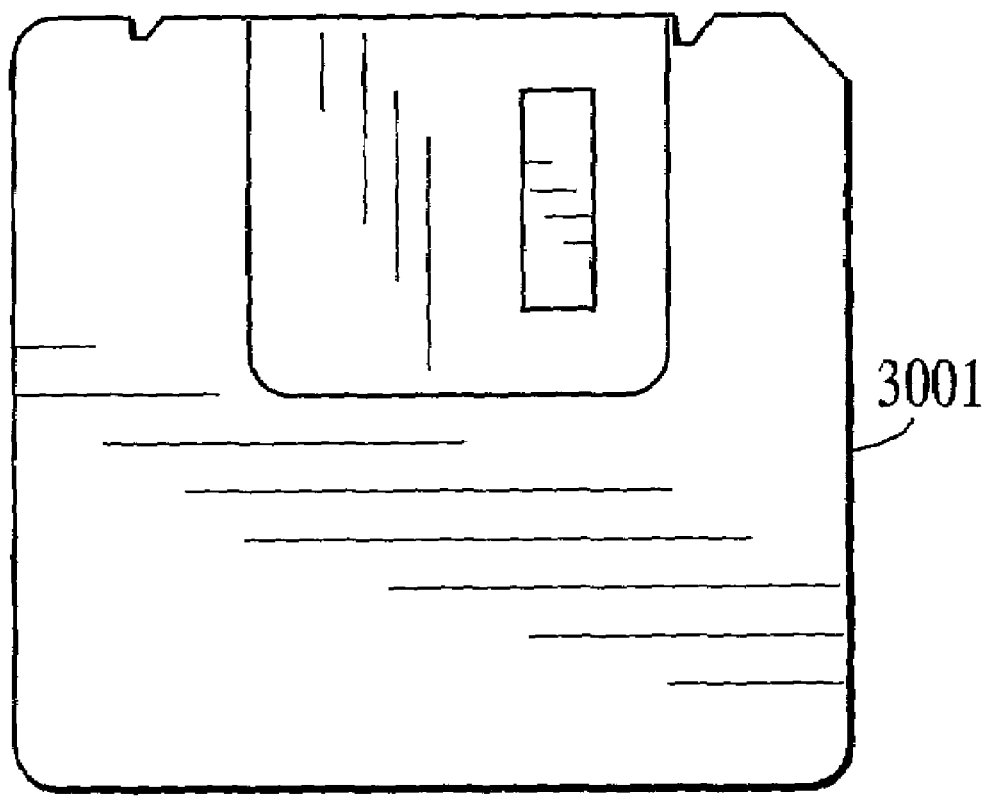
FIG. 31 is an illustration of an exemplary memory medium of a type which can be used with the computer illustrated in FIG. 27.
Figure 32:
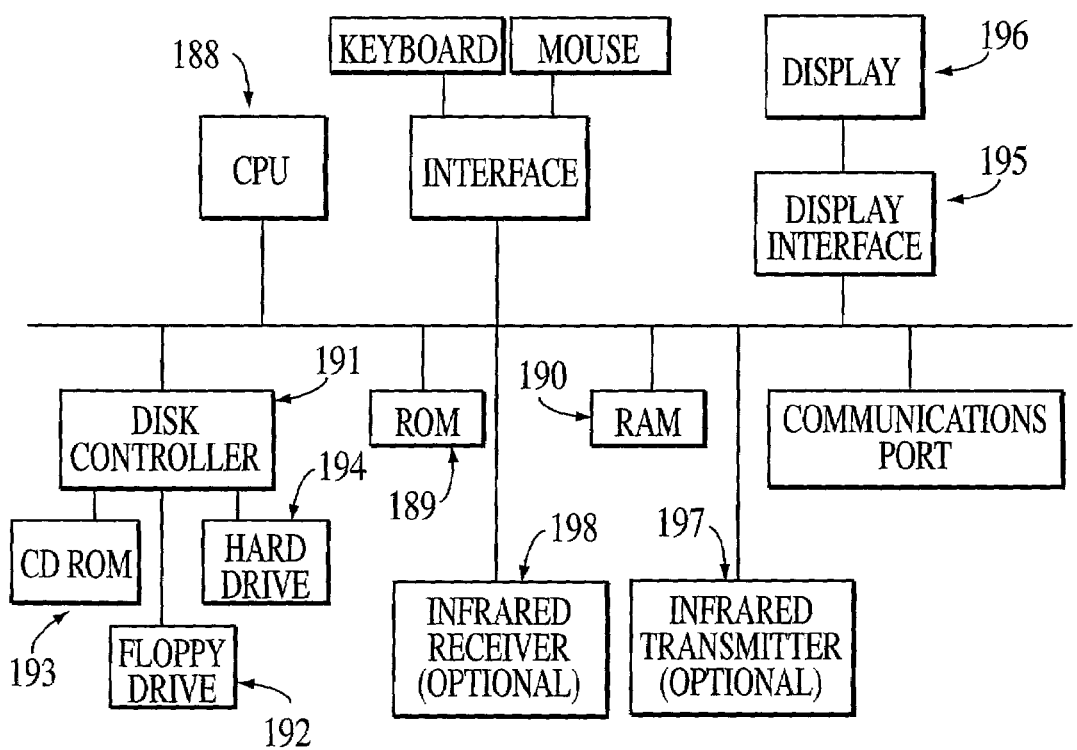
FIG. 32 is a diagram of the conceptual flow of the computer assisted process in accordance with the current invention.
Figure 33:
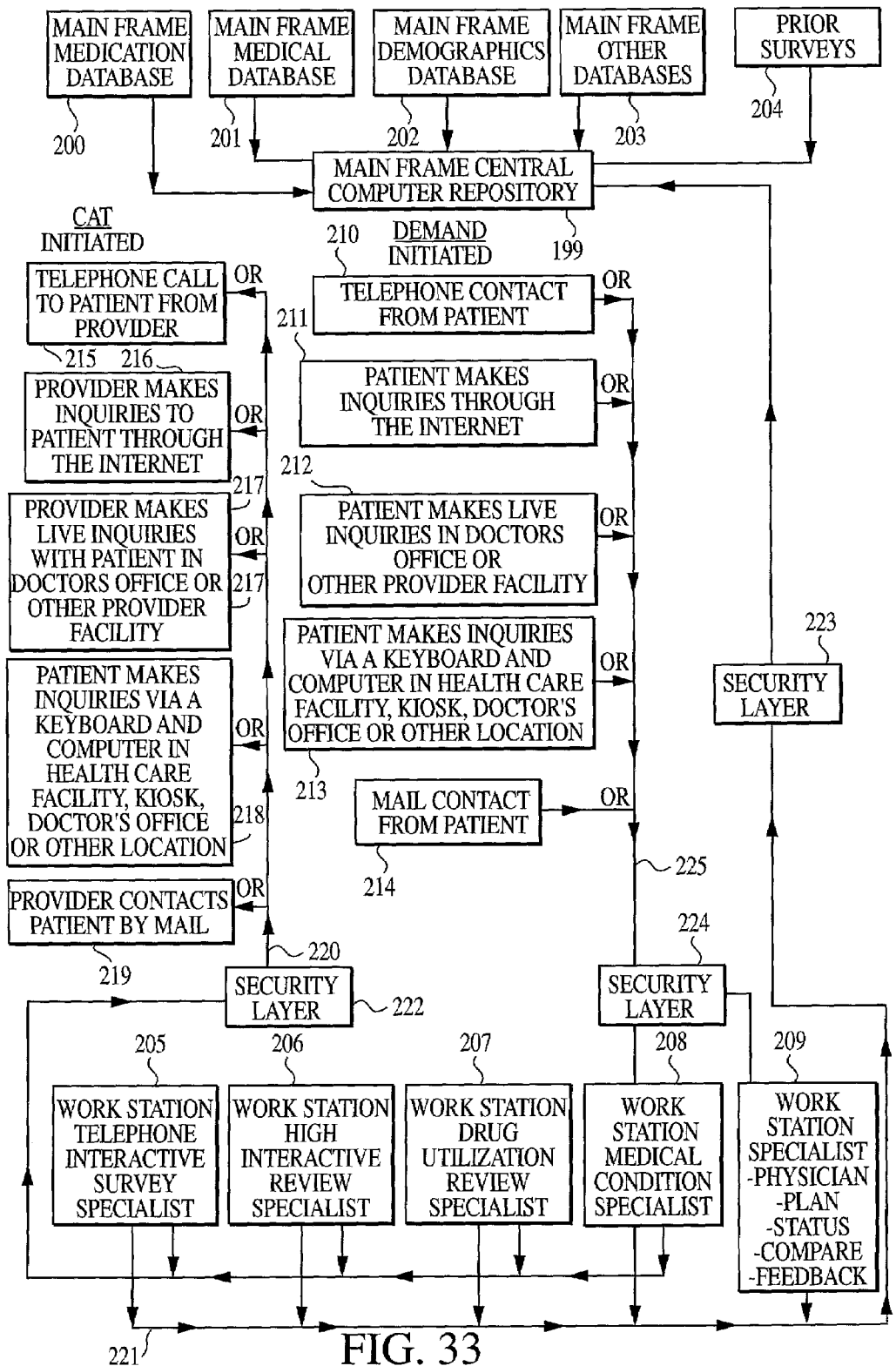
FIG. 33 is a block diagram of the hardware design of the invention in accordance with either the care demand or care assessment embodiment. The figure illustrates the embodiment, for example, using a telephone survey, an internet connection, live interviews, computer interactive response in a health care facility, and the mail.

FIG. 29 is an illustration of the computer system and telephone network used in several embodiments of the invention. FIG. 30 is an illustration of another computer of the type suitable for use in the invention. FIG. 31 is a conceptual view of the memory storage medium. FIG. 32 is a block diagram of standard computer components that make up a standard computer and that may be used in the invention. FIG. 33 is a diagram of another hardware configuration that may be used in the invention.

Hardware Configurations

FIG. 29 is a block diagram of the hardware design of a computer of the type that can be used in the invention. A video adapter board, preferably at VGA or better resolution, interconnects to a video monitor 177. A serial communication circuit 178 interfaces a pointing device, such as a mouse 179. A parallel communication circuit may be used in place of circuit 178 in another embodiment. A keyboard controller circuit 180 interfaces a keyboard 181. A small computer systems interface (SCSI) adapter provides a SCSI bus to which, for example, a 500 Mb or greater hard disk drive is attached. The hard drive 182 stores database files such as the patient files, drug utilization files, and demographic files.

FIG. 30 illustrates another personal computer of the type suitable for carrying out the invention. Viewed externally, the conceptual computer system in FIG. 30 has a central processing unit 183 having disk drives. Disk drive indications 184, 185 are merely symbolic of a number of disk drives which might be accommodated by the computer system. Typically these would include a floppy disk drive 184, a hard disk drive (not shown externally), and a CD ROM. The number and type of drives varies, typically with different computer configurations. Disk drives are in fact optional, and for space considerations, may easily be omitted from the computer system used in conjunction with the processes described herein.

The computer also has an optional display upon which information is displayed. In some situations, a keyboard 186 and a mouse 187 may be provided as input devices to interface with the central processing unit. Then again, for enhanced portability, the keyboard may be either a limited function keyboard or omitted in its entirety. In addition, mouse may be a touch pad control device, or a track ball device, or even omitted in its entirety as well. In addition, the computer system also optionally includes at least one infrared transmitter and/or infrared receiver for either transmitting and/or receiving infrared signals, one example of wireless transmission and/or reception.

FIG. 32 illustrates a block diagram of the internal hardware of the computer of FIG. 30. A bus serves as the main information highway interconnecting the other components of the computer. CPU 188 is the central processing unit of the system, performing calculations and logic operations required to execute a program. Read only memory (ROM) 189 and random access memory (RAM) 190 constitute the main memory of the computer. Disk controller 191 interfaces one or more disk drives to the system bus. These disk drives may be floppy disk drives 192 or CD ROM 193 or DVD (digital video disks) drives such as, internal or external hard drives 194. As indicated previously, these various disk drives and disk controllers are optional devices.

A display interface 195 interfaces the display 196 and permits information from the bus to be displayed on the display 196. Again as indicated, the display is also an optional accessory. For example, the display could be substituted or omitted from the device, and a display on the telephone may be used to display information. Communication with external devices occurs utilizing, for example, the communication port or standard wireless devices.

In addition to the standard components of the computer, the computer also optionally includes an infrared transmitter 197 and/or infrared receiver 198. Infrared transmitter is utilized when the computer system is used in the process described herein. Infrared receiver is generally utilized when the computer system is used in conjunction with the telephone that is to receive the infrared signal. Instead of utilizing an infrared transmitter or infrared receiver, the computer system could use at least one of a low power radio transmitter and/or a low power radio receiver. The low power radio transmitter transmits the signal for reception by another low power radio receiver. The low power radio transmitter and/or receiver are standard devices in industry.

FIG. 31 is an illustration of an exemplary memory medium which can be used with disk drives illustrated in FIGS. 30 and 32. Typically, memory media such as floppy disks, a CD ROM, or a digital video disk will contain, for example, a multi-byte locale for a single byte language and the program information for controlling the computer to enable the computer to perform the functions described herein. Alternatively, ROM 360 and/or RAM 362 illustrated in FIGS. 30 and 32 can also be used to store the program information that is used to instruct the central processing unit to perform the operations associated with the present invention.

FIG. 33 is a block diagram of the hardware design of the present invention in a network environment. In FIG. 33, the system includes main frame or central computer 199 that controls or coordinates requests for receiving and/or storing patient related data, such as including information on: medication 200, patient's physician(s) medical/family history and hospitalization history 201, patient demographics 202, and other relevant data 203 (such as laboratory work), and prior responses to the core survey questions 204, in the central database.

Multiple workstations 205-209 and personnel are optionally provided. The same configuration can be used to administer the core survey in response to patient initiated demand care inquiries 210-216 or provider initiated care assessment tool inquiries 215-219. For example, work station personnel 205 utilizes a workstation to contact the patients 220 via mail 219, a computer key board in a doctors office or kiosk 218, via a live interview with a nurse in a health care providers office 217, via the internet 216, or via a telephone call 215. The work station personnel can collect data therefrom and, as necessary, obtain data from the main frame computer repository 221.

In addition, work station personnel may utilize a workstation so that the personnel can be contacted the patients 225 via mail 214, a computer key board in a doctors office or kiosk 213, via a live interview with a nurse in a health care providers office 212, via the internet 211, or via a telephone call 210. The work station personnel can collect data therefrom, answer questions, administer the core survey, and, as necessary, obtain data from the main frame computer repository 221. Any number of work stations may be used to contact patients and collect data. Other types of communications networks may be used, such as local area networks, coaxial cable systems, wireless, and the like. In addition to contacting the patients, work station personnel connect to the patient profile and the central repository.

Central repository database may comprise a plurality of databases that collectively store the appropriate patient information described above. An optional security layer is also provided to prevent unauthorized access to the central computer 223. Security layers may also be included in the communication between the patient and the work station personnel to protect privacy or for other reasons. The security layer comprises any standard security scheme or technology, such as standard decryption technology, and may be used system wide as well, for example, with all workstations, pharmacist, physicians, and the like. As described above, the present invention does not require the direct interaction with the various computers, but provides this additional feature to further facilitate the communication process between various work station personnel, and the like.

Various other embodiments of the hardware system are possible. For example, an optional voice response unit can also be included to provide mechanized delivery of voice messages. This optional voice response unit may also be utilized in any of the embodiments of the present invention. The optional voice response unit is operative in response to, for example, predetermined messages or questions to be provided to the patient, pharmacist, and/or physician. Voice response unit is also designed to replace any of the above procedures implemented by the caller of the system, in accordance with standard programming techniques. Alternative embodiments include user assisted and/or partially manually assisted and/or completely manual processes.

A major objective and advantage of the present invention is cost reduction (where appropriate, safe, and effective). The entire computer implemented and/or assisted process is centered around the patient's best interest and welfare. The emphasis is on the patient's best interest, which is likely to improve health outcomes and to reduce total health-care expenditures for both the patient and the plan.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An interactive computer assisted method of reviewing, analyzing, and compiling patient profile information from a plurality of different sources into a centralized patient profile database, including an interactive survey designed to evaluate the health status of a health care consumer, said method comprising the steps of:
   (a) developing and updating interactive questions for the interactive survey of the patient to assess the overall health status wherein the survey questions are interactively modified, priority of questions reordered based on answers to the questions, and questions are automatically determined based on previous answers;
   (b) developing and updating rules for determining if the patient is likely to be a high utilization health care consumer;
   (c) periodically accessing the patient profile information from the centralized patient profile database and determining if at least one core survey was completed during a predetermined time interval;
   (d) utilizing the patient profile information stored in the centralized patient profile database and information received in said periodically accessing Step (c) to update core questions, and querying a predetermined number of the patient using at least one of the core survey and the updated core questions to determine if the patient is at risk;
   (e) collecting and storing in a computer storage system patient related information comprising demographic information, health care program availability and eligibility criteria, current health care participation information, patient medical claims, patient drug claims, prior medical history, prior drug usage patterns including nonprescription drug usage, patient behavior factors, and demand management program information;
   (f) interactively evaluating if the patient is likely to be the high utilization health care consumer responsive to said utilizing step (d) and said collecting and storing step (e), and optionally responsive to an outbound communication from a health care representative to the patient;
   (g) determining whether at least one intervention program may reduce health care utilization and improve health of the patient and wherein said determining is automatically executed by a computer analyzing results from said survey and said patient profile;
   (h) determining if the patient is eligible for the at least one intervention program;
   (i) when said determining step (h) determines that the patient is eligible, enrolling the patient in the at least one intervention program or other health care program;
   (j) generating reports on the state of the at least one intervention program responsive to said enrolling step (i), including patient drug utilization, patient evaluation, patient health, comparisons with respect to desired patient health, patient satisfaction, and other information; and
   (k) periodically updating patient profiles, and periodically modifying the rules for determining the risk behaviors for the high utilization health care consumer.

2. An interactive computer assisted method according to claim 1, further comprising the step of (l) conducting the patient survey and assessing whether the patient is a high utilizer of health care services through a direct telephone survey to the patient by a physician, nurse, survey taker or other health care personnel, said conducting step (l) further comprising the steps of:
   (1) determining from a review of the centralized patient profile database which of the patients to call as part of the survey;
   (2) calling the patient and administering the core survey questions;
   (3) interactively evaluating based on the response to the questions, if the patient is the potential high utilization health care consumer;
   (4) determining if there are intervention programs which could reduce utilization and improve health of the patient;

(5) determining if the patient is eligible for such programs;
(6) if eligible, enrolling the patient in the intervention program or other health care program;
(7) generating at least one report;
(8) updating the patient profile and the centralized patient profile database.

3. An interactive computer assisted method according to claim 1, further comprising the step of (l) conducting the patient survey and assessing whether the patient is the high utilization health care consumer through a nurse triage or other demand care telephone call from the patient to a nurse, survey taker or other health care professional, said conducting step (l) further comprises the steps of:
 (1) responding to the specific patient inquiries that caused the patient to call the nurse triage or the other demand care telephone call;
 (2) administering the core survey questions;
 (3) interactively evaluating based on patient response to the core survey questions received in said step (2) whether the patient is the high utilization health care consumer;
 (4) determining whether there are other intervention programs which could reduce utilization and improve health of the patient;
 (5) determining if the patient is eligible for the other intervention programs;
 (6) when eligible, enrolling the patient in the other intervention program;
 (7) generating at least one report; and
 (8) updating the patient profile and the centralized patient profile database.

4. An interactive computer assisted method according to claim 1, further comprising the step of (l) administrating the at least one core survey via a live interview with a nurse, survey taker or other health care professional and assessing whether the patient is the high utilization health care consumer, said administrating step (l) further comprises the steps of:
 (1) interviewing the patient interactively by doctor, nurse, survey taker, or some other health care personnel, in person, telephone or via data connection;
 (2) responding to specific patient inquiries regarding health care conditions;
 (3) administering the at least one core survey;
 (4) interactively evaluating in person, telephone or via data connection based on the response to the questions, if the patient is the high utilization health care consumer;
 (5) determining if there are other intervention programs which could reduce utilization and improve health of the patient;
 (6) determining if the patient is eligible for the other intervention programs;
 (7) when eligible, enrolling the patient in the intervention program or the other intervention program;
 (8) generating at least one report; and
 (9) updating the patient profile and the centralized patient profile database.

5. An interactive computer assisted method according to claim 1, further comprising the step of (l) conducting the at least one core survey and assessing whether the patient is at risk an Internet inquiry from the patient as part of a demand care system, said conducting step (l) comprising the steps of:
 (1) interviewing the patient interactively by doctor, nurse, survey taker, or some other health care via an Internet data connection;
 (2) responding to specific patient inquiries regarding health care conditions via the Internet;
 (3) administering the at least one core survey via the Internet;
 (4) interactively evaluating via the Internet based on the response to the questions, if the patient is the high utilization health care consumer;
 (5) determining if there are other intervention programs which could reduce utilization and improve health of the patient;
 (6) determining if the patient is eligible for the other intervention programs;
 (7) when eligible, enrolling the patient in the intervention program or the other intervention program via the Internet;
 (8) generating at least one report; and
 (9) updating the patient profile and the centralized patient profile database.

6. An interactive computer assisted method according to claim 1, further comprising the step of (l) conducting the at least one core survey and assessing whether the patient is the high utilization health care consumer through patient response using a touch screen or keyboard at a kiosk, physician office, insurance company office or other location, said conducting step (l) comprising the steps of:
 (1) interviewing the patient interactively by doctor, nurse, survey taker, or some other health care via the touch screen or keyboard at the kiosk, the physician office, the insurance company office or the other location;
 (2) responding to specific patient inquiries regarding health care conditions via the touch screen or keyboard at the kiosk, the physician office, the insurance company office or the other location;
 (3) administering the at least one core survey via the touch screen or keyboard at the kiosk, the physician office, the insurance company office or the other location;
 (4) interactively evaluating via the touch screen or keyboard at the kiosk, the physician office, the insurance company office or the other location, based on the response to the questions, if the patient is the high utilization health care consumer;
 (5) determining if there are other intervention programs which could reduce utilization and improve health of the patient;
 (6) determining if the patient is eligible for the other intervention programs;
 (7) when eligible, enrolling the patient in the intervention program or the other intervention program via the touch screen or keyboard at the kiosk, the physician office, the insurance company office or the other location;
 (8) generating at least one report; and
 (9) updating the patient profile and the centralized patient profile database.

7. An interactive computer assisted method according to claim 1, further comprising the step of (l) conducting the at least one core survey and assessing whether the patient is the high utilization health care consumer through a mail survey to the patient or a mail inquiry from the patient including electronic mail, said conducting step (l) further comprising the steps of:
 (1) interviewing the patient interactively by doctor, nurse, survey taker, or some other health care via the mail or electronic mail;
 (2) responding to specific patient inquiries regarding health care conditions via the mail or electronic mail;
 (3) administering the at least one core survey via the mail or electronic mail;

(4) interactively evaluating via the mail or electronic mail based on the response to the questions, if the patient is the high utilization health care consumer;

(5) determining if there are other intervention programs which could reduce utilization and improve health of the patient;

(6) determining if the patient is eligible for the other intervention programs;

(7) when eligible, enrolling the patient in the intervention program or the other intervention program via the mail or electronic mail;

(8) generating at least one report; and (9) updating the patient profile and the centralized patient profile database.

8. An interactive computer assisted method according to claim 1, where when the at least one core survey is administered, the determination of whether the patient is a health risk and potentially a high utilization health care consumer, the availability of health care intervention programs, and the enrollment of the patient in the appropriate program is performed automatically by an automated computer expert system rather than the physician, the nurse, the survey taker, or the other health care personnel.

9. An interactive computer assisted method according to claim 1, where when the at least one core survey is administered, the determination of whether the patient is the high utilization health care consumer, the availability of health care intervention programs, and the enrollment of the patient in the appropriate program is performed with the assistance of an automated computer expert system to be used in conjunction with, or by, the physician, the nurse, the survey taker, or the other health care personnel.

10. An integrated method of reviewing, analyzing, and compiling patient profile information from a plurality of different sources into a centralized patient profile database, including an interactive survey designed to identify high utilization health care consumers, said method comprising the steps of:

(a) developing and updating interactive questions for the interactive survey of the patients to assess the utilization of health care, respectively wherein the survey questions are interactively modified, priority of questions reordered based on answers to the questions, and questions are automatically determined based on previous answers;

(b) developing and updating rules for determining which of the patients are likely to be the high utilization health care consumer;

(c) periodically accessing the patient profile information, drug claims records, self-reported information, medical claims records, general demographic data, eligibility data, and demand for medical services from the centralized patient profile database and determining if at least one core survey was completed during a predetermined time interval, the patient profile information including at least current medications, medication use pattern, over the counter medication use, patient understanding of treatment goals, adverse effects, compliance history, medical history, family history, hospitalization history, pertinent laboratory work, patient demographics, patient behavior and lifestyle risk factor information, and the response to the at least one core survey;

(d) utilizing the patient profile information stored in the centralized patient profile database and information received in said periodically accessing Step (c) to update core questions, and querying a predetermined number of the patients using at least one of the core survey and the updated core questions to determine which of the patients are likely to be the high utilization health care consumers, wherein said querying step further comprises the steps of:

(d1) conducting the patient survey and assessing whether the patient is a high utilizer of health care services through a direct telephone survey to the patient by a physician, nurse, survey taker or other health care personnel;

(d2) conducting the patient survey and assessing whether the patient is the high utilization health care consumer through a nurse triage or other demand care telephone call from the patient to a nurse, survey taker or other health care professional;

(d3) administrating the at least one core survey via a live interview with a nurse, survey taker or other health care professional and assessing whether the patient is the high utilization health care consumer;

(d4) conducting the at least one core survey and assessing whether the patient is the high utilization health care consumer through an internet inquiry from the patient as part of a demand care system;

(d5) conducting the at least one core survey and assessing whether the patient is the high utilization health care consumer through patient response using a touch screen or keyboard at a kiosk, physician office, insurance company office or other location;

(d6) conducting the at least one core survey and assessing whether the patient is the high utilization health care consumer through a mail survey to the patient or a mail inquiry from the patient including electronic mail;

(e) collecting and storing in a computer storage system patient related information comprising demographic information, health care program availability and eligibility criteria, current health care participation information, patient medical claims, patient drug claims, prior medical history, prior drug usage patterns including nonprescription drug usage, patient behavior factors, and demand management program information;

(f) interactively evaluating if the patient is likely to be the high utilization health care consumer responsive to said utilizing step (d) and said collecting and storing step (e), and optionally responsive to an outbound communication from a health care representative to the patient;

(g) determining whether at least one intervention program may reduce health care utilization and improve health of the patient;

(h) determining if the patient is eligible for the at least one intervention program;

(i) when said determining step (h) determines that the patient is eligible, enrolling the patient in the at least one intervention program or other health care program;

(j) generating reports on the state of the at least one intervention program responsive to said enrolling step (i), including patient drug utilization, patient evaluation, patient health, comparisons with respect to desired patient health, patient satisfaction, and other information; and (k) periodically updating member profile and central repository, and periodically modifying the rules for determining the high utilization health care consumer.

11. An interactive computer assisted method according to claim 10, wherein said conducting step (d1) further comprises the steps of:

(1) determining from a review of the centralized patient profile database which patient to call as part of the survey;

(2) calling the patient and administering the core survey questions;
(3) interactively evaluating based on the response to the questions, if the patient is the potential high utilization health care consumer;
(4) determining if there are intervention programs which could reduce utilization and improve health of the patient;
(5) determining if the patient is eligible for such programs;
(6) if eligible, enrolling the patient in the intervention program or other health care program;
(7) generating at least one report;
(8) updating the patient profile and the centralized patient profile database.

12. An interactive computer assisted method according to claim 11, wherein said conducting step (d2) further comprises the steps of:
(1) responding to the specific patient inquiries that caused the patient to call the nurse triage or the other demand care telephone call;
(2) administering the core survey questions;
(3) interactively evaluating based on patient response to the core survey questions received in said step (2) whether the patient is the high utilization health care consumer;
(4) determining whether there are other intervention programs which could reduce utilization and improve health of the patient;
(5) determining if the patient is eligible for the other intervention programs;
(6) when eligible, enrolling the patient in the other intervention program;
(7) generating at least one report; and
(8) updating the patient profile and the centralized patient profile database.

13. An interactive computer assisted method according to claim 12, wherein said administrating step (d3) further comprises the steps of:
(1) interviewing the patient interactively by doctor, nurse, survey taker, or some other health care personnel, in person, telephone or via data connection;
(2) responding to specific patient inquiries regarding health care conditions;
(3) administering the at least one core survey;
(4) interactively evaluating in person, telephone or via data connection based on the response to the questions, if the patient is the high utilization health care consumer;
(5) determining if there are other intervention programs which could reduce utilization and improve health of the patient;
(6) determining if the patient is eligible for the other intervention programs;
(7) when eligible, enrolling the patient in the intervention program or the other intervention program;
(8) generating at least one report; and
(9) updating the patient profile and the centralized patient profile database.

14. An interactive computer assisted method according to claim 13, wherein said conducting step (d4) comprises the steps of:
(1) interviewing the patient interactively by doctor, nurse, survey taker, or some other health care via an Internet data connection;
(2) responding to specific patient inquiries regarding health care conditions via the Internet;
(3) administering the at least one core survey via the Internet;
(4) interactively evaluating via the Internet based on the response to the questions, if the patient is the high utilization health care consumer;
(5) determining if there are other intervention programs which could reduce utilization and improve health of the patient;
(6) determining if the patient is eligible for the other intervention programs;
(7) when eligible, enrolling the patient in the intervention program or the other intervention program via the Internet;
(8) generating at least one report; and
(9) updating the patient profile and the centralized patient profile database.

15. An interactive computer assisted method according to claim 14, wherein said conducting step (d5) comprises the steps of:
(1) interviewing the patient interactively by doctor, nurse, survey taker, or some other health care via the touch screen or keyboard at the kiosk, the physician office, the insurance company office or the other location;
(2) responding to specific patient inquiries regarding health care conditions via the touch screen or keyboard at the kiosk, the physician office, the insurance company office or the other location;
(3) administering the at least one core survey via the touch screen or keyboard at the kiosk, the physician office, the insurance company office or the other location;
(4) interactively evaluating via the touch screen or keyboard at the kiosk, the physician office, the insurance company office or the other location, based on the response to the questions, if the patient is the high utilization health care consumer;
(5) determining if there are other intervention programs which could reduce utilization and improve health of the patient;
(6) determining if the patient is eligible for the other intervention programs;
(7) when eligible, enrolling the patient in the intervention program or the other intervention program via the touch screen or keyboard at the kiosk, the physician office, the insurance company office or the other location;
(8) generating at least one report; and
(9) updating the patient profile and the centralized patient profile database.

16. An interactive computer assisted method according to claim 15, wherein said conducting step (d6) further comprises the steps of:
(1) interviewing the patient interactively by doctor, nurse, survey taker, or some other health care via the mail or electronic mail;
(2) responding to specific patient inquiries regarding health care conditions via the mail or electronic mail;
(3) administering the at least one core survey via the mail or electronic mail;
(4) interactively evaluating via the mail or electronic mail based on the response to the questions, if the patient is the high utilization health care consumer;
(5) determining if there are other intervention programs which could reduce utilization and improve health of the patient;
(6) determining if the patient is eligible for the other intervention programs;
(7) when eligible, enrolling the patient in the intervention program or the other intervention program via the mail or electronic mail;
(8) generating at least one report; and (9) updating the patient profile and the centralized patient profile database.

17. An interactive computer assisted method according to claim 16, where when the at least one core survey is administered, the determination of whether the patient is at risk and potentially a high utilization health care consumer, the availability of health care intervention programs, and the enrollment of the patient in the appropriate program is performed with the assistance of an automated computer expert system rather than the physician, the nurse, the survey taker, or the other health care personnel.

18. An interactive computer assisted method according to claim 16, where when the at least one core survey is administered, the determination of whether the patient is the high utilization health care consumer, the availability of health care intervention programs, and the enrollment of the patient in the appropriate program is performed with the assistance of an automated computer expert system to be used in conjunction with, or by, the physician, the nurse, the survey taker, or the other health care personnel.

19. An interactive computer assisted method of reviewing, analyzing, and compiling patient profile information from a plurality of different sources into a centralized patient profile database, including an interactive survey designed to identify high utilization health care consumers, said method comprising the steps of:
   (a) developing and updating interactive questions for the interactive survey of a patient to assess the utilization of health care, respectively wherein the survey questions are interactively modified, priority of questions reordered based on answers to the questions, and questions are automatically determined based on previous answers;
   (b) developing and updating rules for determining if the patient is likely to be the high utilization health care consumer;
   (c) periodically accessing the patient profile information from the centralized patient profile database and determining if at least one core survey was completed during a predetermined time interval, the patient profile information including at least current medications, medication use pattern, over the counter medication use, patient understanding of treatment goals, adverse effects, compliance history, medical history, family history, hospitalization history, pertinent laboratory work, patient demographics, patient behavior and lifestyle risk factor information, and the response to the at least one core survey;
   (d) utilizing the patient profile information stored in the centralized patient profile database and information received in said periodically accessing Step (c) to update core questions, and querying a predetermined number of the patient using at least one of the core survey and the updated core questions to determine which of the patients are likely to be the high utilization health care consumers;
   (e) collecting and storing in a computer storage system patient related information comprising demographic information, health care program availability and eligibility criteria, current health care participation information, patient medical claims, patient drug claims, prior medical history, prior drug usage patterns including nonprescription drug usage, patient behavior factors, and demand management program information;
   (f) interactively evaluating if the patient is likely to be the high utilization health care consumer responsive to said utilizing step (d) and said collecting and storing step (e), and optionally responsive to an outbound communication from a health care representative to the patient;
   (g) predicting whether at least one intervention program may reduce health care utilization and improve health of the patient;
   (h) determining if the patient is eligible for the at least one intervention program;
   (i) when said determining step (h) determines that the patient is eligible, enrolling the patient in the at least one intervention program or other health care program;
   (j) generating reports on the state of the at least one intervention program responsive to said enrolling step (i), including patient drug utilization, patient evaluation, patient health, comparisons with respect to desired patient health, patient satisfaction, and other information; and
   (k) periodically updating member profile and central repository, and periodically modifying the rules for determining the high utilization health care consumer.

20. An interactive computer assisted method of reviewing, analyzing, and compiling patient profile information from a plurality of different sources into a centralized patient profile database, including an interactive survey designed to evaluate health status and identify high utilization health care consumers, said method comprising at least one of the sequential, non-sequential and sequence independent steps of:
   (a) developing and updating interactive questions for the interactive survey of the patients to assess whether the patient is at least one of a low, medium, and high level utilizer of health care wherein the survey questions are interactively modified, priority of questions reordered based on answers to the questions, and questions are automatically determined based on previous answers;
   (b) developing and updating rules for determining which of the patients are likely to become the high utilization health care consumer responsive to said developing step (a);
   (c) periodically accessing the patient profile information from the centralized patient profile database and optionally determining if at least one core survey was completed during a predetermined time interval, the patient profile information including at least current medications, medication use pattern, over the counter medication use, patient treatment goals, adverse effects, compliance history, medical history, family history, hospitalization history, laboratory work, patient demographics, patient behavior and lifestyle risk factor information, and the response to the at least one core survey;
   (d) utilizing the patient profile information stored in the centralized patient profile database and information received in said periodically accessing Step (c) to optionally update core questions, and optionally querying a predetermined number of the patients using at least one of the core survey and the updated core questions to determine which of the patients are at risk;
   (e) collecting and storing in a computer storage system patient related information comprising demographic information, health care program availability and eligibility criteria, current health care participation information, patient medical claims, patient drug claims, prior medical history, prior drug usage patterns including nonprescription drug usage, patient behavior factors, and demand management program information;
   (f) evaluating if the patient is at risk responsive to said utilizing step (d), and optionally responsive to an outbound communication from a health care representative to the patient and said collecting and storing step (e);

(g) determining whether at least one intervention program may reduce health care utilization and improve health of the patient;

(h) determining if the patient is eligible for the at least one intervention program;

(i) when said determining step (h) determines that the patient is eligible, enrolling the patient in the at least one intervention program or other health care program;

(j) generating reports on the state of the at least one intervention program responsive to said enrolling step (i), including patient drug utilization, patient evaluation, patient health, comparisons with respect to desired patient health, patient satisfaction; and (k) periodically updating member profile, and periodically modifying the rules for determining the high utilization health care consumer.

21. An interactive computer assisted method of reviewing, analyzing, and compiling patient profile information from a plurality of different sources into a centralized patient profile database, including an interactive survey designed to identify high utilization health care consumers, said method comprising at least one of the sequential, non-sequential and sequence independent steps of:

(a1) developing and updating interactive questions for the interactive survey of the patients to assess the utilization of health care wherein the survey questions are interactively modified, priority of questions reordered based on answers to the questions, and questions are automatically determined based on previous answers;

(a2) conducting the at least one core survey and assessing whether the patient is at risk an Internet inquiry from the patient as part of a demand care system, said conducting step (k) comprising the steps of:

(1) interviewing the patient interactively by doctor, nurse, survey taker, or some other health care via an Internet data connection;

(2) responding to specific patient inquiries regarding health care conditions via the Internet;

(3) administering the at least one core survey via the Internet;

(4) interactively evaluating via the Internet based on the response to the questions, if the patient is the high utilization health care consumer;

(5) determining if there are other intervention programs which could reduce utilization and improve health of the patient;

(6) determining if the patient is eligible for the other intervention programs;

(7) when eligible, enrolling the patient in the intervention program or the other intervention program via the Internet;

(8) generating at least one report; and (9) updating the patient profile and the centralized patient profile database;

(b) developing and updating rules for determining which of the patients are likely to be the high utilization health care consumer responsive to said developing step (a);

(c) accessing the patient profile information, drug claims records, self-reported information, medical claims records, general demographic data, eligibility data, and demand for medical services from the centralized patient profile database and determining if at least one core survey was completed during a predetermined time interval, the patient profile information including at least current medications, medication use pattern, over the counter medication use, patient treatment goals, adverse effects, compliance history, medical history, family history, hospitalization history, laboratory work, patient demographics, patient behavior and lifestyle risk factor information, and the response to the at least one core survey;

(d) utilizing the patient profile information stored in the centralized patient profile database and information received in said accessing Step (c) to update core questions, and querying a predetermined number of the patients using the core survey and the updated core questions to determine which of the patients are likely to be the high utilization health care consumers;

(e) collecting and storing in a computer storage system patient related information comprising demographic information, health care program availability and eligibility criteria, current health care participation information, patient medical claims, patient drug claims, prior medical history, prior drug usage patterns including nonprescription drug usage, patient behavior factors, and demand management program information;

(f) predicting if the patient is likely to be the high utilization health care consumer responsive to said utilizing step (d) and said collecting and storing step (e), and responsive to an outbound communication from a health care representative to the patient and wherein said predicting is accomplished by a computer analyzing the centralized patient profile database, wherein the predicting if the patient is likely to be high utilization health care consumer, the availability of health care intervention programs, and the enrollment of the patient in the appropriate program is performed with the assistance of an automated computer expert system to be used in conjunction with, or by, the physician, the nurse, the survey taker, or the other health care personnel; and (g) automatically presenting to the patient at least one of an intervention program, drug therapy program, and therapy program predicted by the computer to reduce health care utilization and improve health of the patient.

* * * * *